(12) United States Patent
Lustbader et al.

(10) Patent No.: US 7,442,684 B2
(45) Date of Patent: Oct. 28, 2008

(54) LONG-ACTING HORMONE AND GROWTH FACTOR COMPOSITIONS AND USES THEREOF

(75) Inventors: Joyce Lustbader, Tenafly, NJ (US); Leslie Lobel, Forest Hills, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 181 days.

(21) Appl. No.: 10/357,253

(22) Filed: Jan. 31, 2003

(65) Prior Publication Data

US 2003/0216313 A1 Nov. 20, 2003

Related U.S. Application Data

(63) Continuation-in-part of application No. 10/119,427, filed on Apr. 9, 2002, now Pat. No. 7,173,113, which is a continuation-in-part of application No. 10/062,931, filed on Jan. 31, 2002, now abandoned.

(51) Int. Cl.
*A61K 38/00* (2006.01)
*A61K 38/24* (2006.01)
*A61K 38/16* (2006.01)
*C07K 1/00* (2006.01)

(52) U.S. Cl. .............................. 514/12; 514/8; 530/399; 530/397

(58) Field of Classification Search ....................... None
See application file for complete search history.

(56) References Cited

U.S. PATENT DOCUMENTS

| | | | |
|---|---|---|---|
| 4,179,337 A | 12/1979 | Davis | |
| 5,585,345 A | 12/1996 | Boime | 514/8 |
| 5,712,122 A | 1/1998 | Boime et al. | |
| 5,759,818 A | 6/1998 | Boime | 435/69.7 |
| 5,958,737 A | 9/1999 | Boime et al. | |
| 5,985,611 A | 11/1999 | Boime | 435/69.4 |
| 6,040,157 A * | 3/2000 | Hu et al. | 435/69.4 |
| 6,225,449 B1 | 5/2001 | Boime | 530/399 |
| 6,242,580 B1 | 6/2001 | Boime et al. | 530/398 |
| 6,306,654 B1 | 10/2001 | Boime et al. | 435/360 |
| 7,173,113 B2 | 2/2007 | Lustbader et al. | |

FOREIGN PATENT DOCUMENTS

WO WO 03/064619 A2 8/2003

OTHER PUBLICATIONS

Gabrilovich et al. 2003. Chapter 44 in the Cytokine Handbook, 4th edition. Ed: Thomson et al. Academic Press, pp. 1017-1034.*
Backer et al. 2001. Protein Expression and Purification 23:1-7.*
Arora N. et al. 1999. Cancer Res. 59:183-188.*
Halin C et al. 2002. Int J Cancer 102:109-116.*

International Search Report issued Dec. 1, 2003 in connection with PCT International Application No. PCT/US03/02982: and.

Ben-Menahem et al. (2001) The Position of the Alpha and Beta Subunits in a Single Chain Variant of Human Chorionic Gonadotropin Affects the Heterodimeric Interaction of the Subunits and Receptor-Binding Epitope. J. Biol. Chem. 276:29871-879.

Bouloux, P. M. et al. (2001) First human exposure to FSH-CTP in hypogonadotrophic hypogonadal males. *Hum. Reprod.* 16, 1592-1597.

Calvo, F. O. et al. (1986) Deglycosylated human follitropin: characterization and effects on adenosine cyclic 3', 5'-phosphate production in porcine granulosa cells. *Biochemistry* 25, 3938-3943.

Chui, D. K. et al. (1997) Follicular vascularity—the predictive value of transvaginal power Doppler ultrasonography in an in vitro fertilization programme: a preliminary study. *Hum. Reprod.* 12, 191-196.

Dissen, G. A. et al. Ojeda (1994) Immature rat ovaries become revascularized rapidly after autotransplantation and show a gonadotropin-dependent increase in angiogenic factor gene expression. *Endocrinology* 134, 1146-1154.

Fares, F. A. et al. (1992) Design of a long-acting follitropin agonist by fusing the C-terminal sequence of the chorionic gonadotropin beta subunit to the follitropin beta subunit. *Proc. Natl. Acad. Sci U.S.A.* 89, 4304-4308.

Feng, W. et al. (1995) The asparagine-linked oligosaccharides of the human chorionic gonadotropin beta subunit facilitate correct disulfide bond pairing. *J. Biol. Chem.* 270, 11851-11859.

Ferrara, N. et al. (1998) Vascular endothelial growth factor is essential for corpus luteum angiogenesis. *Nat. Med.* 4, 336-340.

Ferrara, N. et al. (1992) Molecular and biological properties of the vascular endothelial growth factor family of proteins. *Endocr. Rev.* 13, 18-32.

Krichevsky, A. et al. (1994) The development of a panel of monoclonal antibodies to human luteinizing hormone and its application to immunological mapping and two-site assays. *Endocrine* 2. 511-520.

LeContonnec, J.Y. et al. (1994) Clinical pharmacology of recombinant human follicle-stimulating hormone. II. Single doses and steady-state pharmacokinetics. *Fertil. Steril.* 61, 679-86.

Lindau-Shapard, B. A. et al. (2001) Reversible immunoneutralization of human follitropin receptor. *J. Reprod. Immun.* 49, 1-19.

(Continued)

*Primary Examiner*—Manjunath Rao
*Assistant Examiner*—Shulamith H Shafer
(74) *Attorney, Agent, or Firm*—John P. White; Cooper & Dunham LLP

(57) ABSTRACT

This invention provides VEGF-FSH compounds having increased serum half-lives relative to either native VEGF or FSH, in which both VEGF and FSH are biologically active. This invention also provides related compositions and methods for increasing fertility, egg production and spermatogenesis in a subject, as well as methods for increasing vascularization in a tissue, particularly in ovarian tissue.

1 Claim, 23 Drawing Sheets

OTHER PUBLICATIONS

Matzuk, M. M. et al. (1990) The biological role of the carboxyl-terminal extension of human chorionic gonadotropin beta-subunit. *Endocrinology 126*, 376-383.

Nargund, G. et al. (1996) Associations between ultrasound indices of follicular blood flow, oocyte recovery and preimplantation embryo quality. *Hum. Reprod. 11*, 109-113.

Pedersen, T. and H. Peters (1968) Proposal for a classification of oocytes and follicles in the mouse ovary. *J. Reprod. Fertil. 17*, 555-557.

Pierce, J. G. and T. F. Parsons (1981) Glycoprotein hormones: structure and function. *Annu. Rev. Biochem. 50*, 465-495.

Porchet, H.C. et al. (1995) Pharmacokinetics of recombinant human luteinizing hormone. *J. Clin. Endocrinol. Metab. 80*, 667-73.

Saal, W. et al. (1991) Pharmacodynamics and pharmacokinetics after subcutaneous and intramuscular injection of human chorionic gonadotropin. *Fertil. Steril. 56*, 225-8.

Sairam, M. R. and P. Manjunath (1982) Studies on pituitary follitropin. XL Induction of hormonal antagonistic activity by chemical deglycosylation. *Mol. Cell Endocrinol. 28*, 139-150.

Sugahara, T. et al. (1996) Characterization of the O-glycosylation sites in the chorionic gonadotropin beta subunit in vivo using site-directed mutagenesis and gene transfer. *J. Biol. Chem. 271*, 20797-20804.

Suganuma, N. et al. (1989) Elimination of disulfide bonds affects assembly and secretion of the human chorionic gonadotropin beta subunit. *J. Biol. Chem. 264*, 19302-19307.

Van Blerkom, J. et al. (1997) The developmental potential of the human oocyte is related to the dissolved oxygen content of follicular fluid: association with vascular endothelial growth factor levels and perifollicular blood flow characteristics. *Hum. Reprod. 12*, 1047-1055.

Yen, S. S. et al. (1968) Disappearance rates of endogenous luteinizing hormone and chorionic gonadotropin in man. *J. Clin. Endocrinol. Metab. 28*, 1763-1767.

U.S. Appl. No. 10/062,931, filed Jan. 31, 2002, Joyce Lustbader et al.

Amendment submitted Feb. 22, 2005 in connection with U.S. Appl. No. 10/119,427, filed Apr. 9, 2002.

Amendment submitted May 16, 2005 in connection with U.S. Appl. No. 10/119,427, filed Apr. 9, 2002.

Amendment submitted Oct. 19, 2005 in connection with U.S. Appl. No. 10/119,427, filed Apr. 9, 2002.

Amendment submitted Jun. 5, 2006 in connection with U.S. Appl. No. 10/119,427, filed Apr. 9, 2002.

Amendment submitted Aug. 18, 2006 in connection with U.S. Appl. No. 10/119,427, filed Apr. 9, 2002.

Interview Summary included with the Notice of Allowance issued Sep. 14, 2006 in connection with U.S. Appl. No. 10/119,427, filed Apr. 9, 2002.

Invitation to Pay Additional Fees issued Sep. 5, 2003 in connection with PCT International Application No. PCT/US03/02982, filed Jan. 31, 2003.

Notification of Transmittal of the International Search Report or the Declaration, including International Search Report issued Dec. 1, 2003 in connection with PCT International Application No. PCT/US03/02982, filed Jan. 31, 2003.

Office Action issued Jan. 19, 2005 in connection with U.S. Appl. No. 10/119,427, filed Apr. 9, 2002.

Office Action issued Jul. 19, 2005 in connection with U.S. Appl. No. 10/119,427, filed Apr. 9, 2002.

Office Action issued Feb. 3, 2006 in connection with U.S. Appl. No. 10/119,427, filed Apr. 9, 2002.

Response to Sep. 5, 2003 Invitation to Pay Additional Fees submitted Sep. 18, 2003 in connection with PCT International Application No. PCT/US03/02982, filed Jan. 31, 2003.

Substitute Notice of Allowability, including Detailed Action and Interview Summaries issued Oct. 2, 2006 in connection with U.S. Appl. No. 10/119,427, filed Apr. 9, 2002.

\* cited by examiner

Figure 1

```
atg aag aca ctc cag ttt ttc ttc ctt ttc tgt tgc tgg aaa gca atc
48
Met Lys Thr Leu Gln Phe Phe Phe Leu Phe Cys Cys Trp Lys Ala Ile
1                5               10              15 tgc tgc aat agc tgt gag ctg acc aac atc acc att gca ata gag aaa
96
Cys Cys Asn Ser Cys Glu Leu Thr Asn Ile Thr Ile Ala Ile Glu Lys
            20              25              30 gaa gaa tgt cgt ttc tgc ata agc atc aac acc act tgg tgt gct ggc
144
Glu Glu Cys Arg Phe Cys Ile Ser Ile Asn Thr Thr Trp Cys Ala Gly
        35              40              45 tac tgc tac acc agg gat ctg gta tat aag gac cca gcc agg ccc aaa
192
Tyr Cys Tyr Thr Arg Asp Leu Val Tyr Lys Asp Pro Ala Arg Pro Lys
    50              55              60 atc cag aaa aca tgt acc ttc aag gaa ctg gta tat gaa aca gtg aga
240
Ile Gln Lys Thr Cys Thr Phe Lys Glu Leu Val Tyr Glu Thr Val Arg
65              70              75              80 gtg ccc ggc tgt gct cac cat gca gat tcc ttg tat aca tac cca gtg
288
Val Pro Gly Cys Ala His His Ala Asp Ser Leu Tyr Thr Tyr Pro Val
                85              90              95 gcc acc cag tgt cac tgt ggc aag tgt gac agc gac agc act gat tgt
336
Ala Thr Gln Cys His Cys Gly Lys Cys Asp Ser Asp Ser Thr Asp Cys
            100             105             110 act gtg cga ggc ctg ggg ccc agc tac tgc tcc ttt ggt gaa atg aaa
384
Thr Val Arg Gly Leu Gly Pro Ser Tyr Cys Ser Phe Gly Glu Met Lys
        115             120             125 gaa gga tcc gga tcg aac gcg acg ggg tca ggt tct aat gca act tca
432
Glu Gly Ser Gly Ser Asn Ala Thr Gly Ser Gly Ser Asn Ala Thr Ser
    130             135             140 gga tcc taa
            441
Gly Ser
145
```

Figure 2

```
atg aag aca ctc cag ttt ttc ttc ctt ttc tgt tgc tgg aaa gca atc
48
Met Lys Thr Leu Gln Phe Phe Phe Leu Phe Cys Cys Trp Lys Ala Ile
1               5               10                  15 tgc tgc aat agc tgt gag ctg acc aac atc acc att gca ata gag aaa
96
Cys Cys Asn Ser Cys Glu Leu Thr Asn Ile Thr Ile Ala Ile Glu Lys
            20              25                  30 gaa gaa tgt cgt ttc tgc ata agc atc aac acc act tgg tgt gct ggc
144
Glu Glu Cys Arg Phe Cys Ile Ser Ile Asn Thr Thr Trp Cys Ala Gly
        35              40              45 tac tgc tac acc agg gat ctg gcg tat aag gac cca gcc agg ccc aaa
192
Tyr Cys Tyr Thr Arg Asp Leu Val Tyr Lys Asp Pro Ala Arg Pro Lys
    50              55              60 atc cag aaa aca tgt acc ttc aag gaa ctg gta tat gaa aca gtg aga
240
Ile Gln Lys Thr Cys Thr Phe Lys Glu Leu Val Tyr Glu Thr Val Arg
65              70              75              80 gtg ccc ggc tgt gct cac cat gca gat tcc ttg tat aca tac cca gtg
288
Val Pro Gly Cys Ala His His Ala Asp Ser Leu Tyr Thr Tyr Pro Val
                85              90                  95 gcc acc cag tgt cac tgt ggc aag tgt gac agc gac agc act gat tgt
336
Ala Thr Gln Cys His Cys Gly Lys Cys Asp Ser Asp Ser Thr Asp Cys
            100             105                 110 act gtg cga ggc ctg ggg ccc agc tac tgc tcc ttt ggt gaa atg aaa
384
Thr Val Arg Gly Leu Gly Pro Ser Tyr Cys Ser Phe Gly Glu Met Lys
            115             120                 125 gaa gga tcc gga tcg aac gcg acg ggg tca ggt tct aat gca act tca
432
Glu Gly Ser Gly Ser Asn Ala Thr Gly Ser Gly Ser Asn Ala Thr Ser
        130             135                 140 aga tcc gga tcg aac gcg acg ggg tca ggt tct aat gca act tca gga
480
Arg Ser Gly Ser Asn Ala Thr Gly Ser Gly Ser Asn Ala Thr Ser Gly
145             150                 155                 160 tcc taa
            486
Ser
```

Figure 3

```
atg aag aca ctc cag ttt ttc ttc ctt ttc tgt tgc tgg aaa gca atc        48
Met Lys Thr Leu Gln Phe Phe Phe Leu Phe Cys Cys Trp Lys Ala Ile
1               5                   10                  15 tgc tgc aat agc tgt gag ctg acc aac atc acc att gca ata gag aaa        96
Cys Cys Asn Ser Cys Glu Leu Thr Asn Ile Thr Ile Ala Ile Glu Lys
            20                  25                  30 gaa gaa tgt cgt ttc tgc ata agc atc aac acc act tgg tgt gct ggc       144
Glu Glu Cys Arg Phe Cys Ile Ser Ile Asn Thr Thr Trp Cys Ala Gly
        35                  40                  45 tac tgc tac acc agg gat ctg gta tat aag gac cca gcc agg ccc aaa       192
Tyr Cys Tyr Thr Arg Asp Leu Val Tyr Lys Asp Pro Ala Arg Pro Lys
    50                  55                  60 atc cag aaa aca tgt acc ttc aag gaa ctg gta tat gaa aca gtg aga       240
Ile Gln Lys Thr Cys Thr Phe Lys Glu Leu Val Tyr Glu Thr Val Arg
65                  70                  75                  80 gtg ccc ggc tgt gct cac cat gca gat tcc ttg tat aca tac cca gtg       288
Val Pro Gly Cys Ala His His Ala Asp Ser Leu Tyr Thr Tyr Pro Val
                85                  90                  95 gcc acc cag tgt cac tgt ggc aag tgt gac agc gac agc act gat tgt       336
Ala Thr Gln Cys His Cys Gly Lys Cys Asp Ser Asp Ser Thr Asp Cys
            100                 105                 110 act gtg cga ggc ctg ggg ccc agc tac tgc tcc ttt ggt gaa atg aaa       384
Thr Val Arg Gly Leu Gly Pro Ser Tyr Cys Ser Phe Gly Glu Met Lys
        115                 120                 125 gaa gga tcc ccc cgc ttc cag gac tcc tct tca aag gcc cct ccc           432
Glu Gly Ser Pro Arg Phe Gln Asp Ser Ser Ser Lys Ala Pro Pro
    130                 135                 140 ccc agc ctt cca agc cca tcc cga ctc ccg ggg ccc tcg gac acc ccg       480
Pro Ser Leu Pro Ser Pro Ser Arg Leu Pro Gly Pro Ser Asp Thr Pro
145                 150                 155                 160 atc ctc cca caa act agt gct cct gat gtg cag gat tgc cca gaa tgc       528
Ile Leu Pro Gln Thr Ser Ala Pro Asp Val Gln Asp Cys Pro Glu Cys
                165                 170                 175 acg cta cag gaa aac cca ttc ttc tcc cag ccg ggt gcc cca ata ctt       576
Thr Leu Gln Glu Asn Pro Phe Phe Ser Gln Pro Gly Ala Pro Ile Leu
            180                 185                 190 cag tgc atg ggc tgc tgc ttc tct aga gca tat ccc act cca cta agg       624
Gln Cys Met Gly Cys Cys Phe Ser Arg Ala Tyr Pro Thr Pro Leu Arg
        195                 200                 205 tcc aag aag acg atg ttg gtc caa aag aac gtc acc tca gag tcc act       672
Ser Lys Lys Thr Met Leu Val Gln Lys Asn Val Thr Ser Glu Ser Thr
    210                 215                 220 tgc tgt gta gct aaa tca tat aac agg gtc aca gta atg ggg ggt ttc       720
Cys Cys Val Ala Lys Ser Tyr Asn Arg Val Thr Val Met Gly Gly Phe
225                 230                 235                 240 aaa gtg gag aac cac acg gcg tgc cac tgc agt act tgt tat tat cac       768
Lys Val Glu Asn His Thr Ala Cys His Cys Ser Thr Cys Tyr Tyr His
                245                 250                 255 aaa tct taa                                                           777
Lys Ser
```

Figure 4

```
atg aag aca ctc cag ttt ttc ttc ctt ttc tgt tgc tgg aaa gca atc
48
Met Lys Thr Leu Gln Phe Phe Phe Leu Phe Cys Cys Trp Lys Ala Ile
1               5                   10                  15 tgc tgc aat agc tgt gag ctg acc aac atc acc att gca ata gag aaa
96
Cys Cys Asn Ser Cys Glu Leu Thr Asn Ile Thr Ile Ala Ile Glu Lys
            20              25              30 gaa gaa tgt cgt ttc tgc ata agc atc aac acc act tgg tgt gct ggc
144
Glu Glu Cys Arg Phe Cys Ile Ser Ile Asn Thr Thr Trp Cys Ala Gly
        35              40              45 tac tgc tac acc agg gat ctg gtg tat aag gac cca gcc agg ccc aaa
192
Tyr Cys Tyr Thr Arg Asp Leu Val Tyr Lys Asp Pro Ala Arg Pro Lys
    50              55              60 atc cag aaa aca tgt acc ttc aag gaa ctg gta tat gaa aca gtg aga
240
Ile Gln Lys Thr Cys Thr Phe Lys Glu Leu Val Tyr Glu Thr Val Arg
65              70              75                  80 gtg ccc ggc tgt gct cac cat gca gat tcc ttg tat aca tac cca gtg
288
Val Pro Gly Cys Ala His His Ala Asp Ser Leu Tyr Thr Tyr Pro Val
            85              90              95 gcc acc cag tgt cac tgt ggc aag tgt gac agc gac agc act gat tgt
336
Ala Thr Gln Cys His Cys Gly Lys Cys Asp Ser Asp Ser Thr Asp Cys
        100             105             110 act gtg cga ggc ctg ggg ccc agc tac tgc tcc ttt ggt gaa atg aaa
384
Thr Val Arg Gly Leu Gly Pro Ser Tyr Cys Ser Phe Gly Glu Met Lys
    115             120             125 gaa gga tcc gga tcg aac gcg acg ggg tca ggt tct aat gca act tca
432
Glu Gly Ser Gly Ser Asn Ala Thr Gly Ser Gly Ser Asn Ala Thr Ser
130             135             140 gga tcc act agt gct cct gat gtg cag gat tgc cca gaa tgc acg cta
480
Gly Ser Thr Ser Ala Pro Asp Val Gln Asp Cys Pro Glu Cys Thr Leu
145             150             155             160 cag gaa aac cca ttc ttc tcc cag ccg ggt gcc cca ata ctt cag tgc
528
Gln Glu Asn Pro Phe Phe Ser Gln Pro Gly Ala Pro Ile Leu Gln Cys
        165             170             175 atg ggc tgc tgc ttc tct aga gca tat ccc act cca cta agg tcc aag
576
Met Gly Cys Cys Phe Ser Arg Ala Tyr Pro Thr Pro Leu Arg Ser Lys
    180             185             190 aag acg atg ttg gtc caa aag aac gtc acc tca gag tcc act tgc tgt
624
Lys Thr Met Leu Val Gln Lys Asn Val Thr Ser Glu Ser Thr Cys Cys
        195             200             205 gta gct aaa tca tat aac agg gtc aca gta atg ggg ggt ttc aaa gtg
672
Val Ala Lys Ser Tyr Asn Arg Val Thr Val Met Gly Gly Phe Lys Val
    210             215             220 gag aac cac acg gcg tgc cac tgc agt act tgt tat tat cac aaa tct
720
Glu Asn His Thr Ala Cys His Cys Ser Thr Cys Tyr Tyr His Lys Ser
225             230             235             240 taa
723
```

Figure 5

```
atg aag aca ctc cag ttt ttc ttc ctt ttc tgt tgc tgg aaa gca atc        48
Met Lys Thr Leu Gln Phe Phe Phe Leu Phe Cys Cys Trp Lys Ala Ile
1               5                   10                  15 tgc tgc aat agc tgt gag ctg acc aac atc acc att gca ata gag aaa        96
Cys Cys Asn Ser Cys Glu Leu Thr Asn Ile Thr Ile Ala Ile Glu Lys
            20                  25                  30 gaa gaa tgt cgt ttc tgc ata agc atc aac acc act tgg tgt gct ggc       144
Glu Glu Cys Arg Phe Cys Ile Ser Ile Asn Thr Thr Trp Cys Ala Gly
        35                  40                  45 tac tgc tac acc agg gat ctg gtg tat aag gac cca gcc agg ccc aaa       192
Tyr Cys Tyr Thr Arg Asp Leu Val Tyr Lys Asp Pro Ala Arg Pro Lys
    50                  55                  60 atc cag aaa aca tgt acc ttc aag gaa ctg gta tat gaa aca gtg aga       240
Ile Gln Lys Thr Cys Thr Phe Lys Glu Leu Val Tyr Glu Thr Val Arg
65                  70                  75                  80 gtg ccc ggc tgt gct cac cat gca gat tcc ttg tat aca tac cca gtg       288
Val Pro Gly Cys Ala His His Ala Asp Ser Leu Tyr Thr Tyr Pro Val
                85                  90                  95 gcc acc cag tgt cac tgt ggc aag tgt gac agc gac agc act gat tgt       336
Ala Thr Gln Cys His Cys Gly Lys Cys Asp Ser Asp Ser Thr Asp Cys
            100                 105                 110 act gtg cga ggc ctg ggg ccc agc tac tgc tcc ttt ggt gaa atg aaa       384
Thr Val Arg Gly Leu Gly Pro Ser Tyr Cys Ser Phe Gly Glu Met Lys
        115                 120                 125 gaa gga tcc gga tcg aac gcg acg ggg tca ggt tct aat gca act tca       432
Glu Gly Ser Gly Ser Asn Ala Thr Gly Ser Gly Ser Asn Ala Thr Ser
    130                 135                 140 aga tcc gga tcg aac gcg acg ggg tca ggt tct aat gca act tca gga       480
Arg Ser Gly Ser Asn Ala Thr Gly Ser Gly Ser Asn Ala Thr Ser Gly
145                 150                 155                 160 tcc act agt gct cct gat gtg cag gat tgc cca gaa tgc acg cta cag       528
Ser Thr Ser Ala Pro Asp Val Gln Asp Cys Pro Glu Cys Thr Leu Gln
                165                 170                 175 gaa aac cca ttc ttc tcc cag ccg ggt gcc cca ata ctt cag tgc atg       576
Glu Asn Pro Phe Phe Ser Gln Pro Gly Ala Pro Ile Leu Gln Cys Met
            180                 185                 190 ggc tgc tgc ttc tct aga gca tat ccc act cca cta agg tcc aag aag       624
Gly Cys Cys Phe Ser Arg Ala Tyr Pro Thr Pro Leu Arg Ser Lys Lys
        195                 200                 205 acg atg ttg gtc caa aag aac gtc acc tca gag tcc act tgc tgt gta       672
Thr Met Leu Val Gln Lys Asn Val Thr Ser Glu Ser Thr Cys Cys Val
    210                 215                 220 gct aaa tca tat aac agg gtc aca gta atg ggg ggt ttc aaa gtg gag       720
Ala Lys Ser Tyr Asn Arg Val Thr Val Met Gly Gly Phe Lys Val Glu
225                 230                 235                 240 aac cac acg gcg tgc cac tgc agt act tgt tat tat cac aaa tct taa       768
Asn His Thr Ala Cys His Cys Ser Thr Cys Tyr Tyr His Lys Ser
                245                 250                 255
```

Figure 12

Beta hCG

```
1                                            10             CHO
Ser-Lys-Glu-Pro-Leu-Arg-Pro-Arg-Cys-Arg-Pro-Ile-Asn-Ala-Thr-Leu-Ala-
         20                                     CHO
Val-Glu-Lys-Glu-Gly-Cys-Pro-Val-Cys-Ile-Thr-Val-Asn-Thr-Thr-Ile-Cys-
              40                                              50
Ala-Gly-Tyr-Cys-Pro-Thr-Met-Thr-Arg-Val-Leu-Gln-Gly-Val-Leu-Pro-Ala-
                         60
Leu-Pro-Gln-Val-Val-Cys-Asn-Tyr-Arg-Asp-Val-Arg-Phe-Glu-Ser-Ile-Arg-
     70                                    80
Leu-Pro-Gly-Cys-Pro-Arg-Gly-Val-Asn-Pro-Val-Val-Ser-Tyr-Ala-Val-Ala-
              90                                           100
Leu-Ser-Cys-Gln-Cys-Ala-Leu-Cys-Arg-Arg-Ser-Thr-Thr-Asp-Cys-Gly-Gly-
                              110
Pro-Lys-Asp-His-Pro-Leu-Thr-Cys-Asp-Asp-Pro-Arg-Phe-Gln-Asp-Ser-Ser-
120     CHO                         CHO        130     CHO
Ser-Ser-Lys-Ala-Pro-Pro-Pro-Ser-Leu-Pro-Ser-Pro-Ser-Arg-Leu-Pro-Gly-
    CHO      140                145
Pro-Ser-Asp-Thr-Pro-Ile-Leu-Pro-Gln
```

Figure 15

```
      M   K   T   L   Q   F   F   F   L   F   C   C   W
  1   atg aag aca ctc cag ttt ttc ttc ctt ttc tgt tgc tgg   39

K   A   I   C   C   N   S   C   E   L   T   N   I
 40   aaa gca atc tgc tgc aat agc tgt gag ctg acc aac atc   78

T   I   A   I   E   K   E   E   C   R   F   C   I
 79   acc att gca ata gag aaa gaa gaa tgt cgt ttc tgc ata   117

S   I   N   T   T   W   C   A   G   Y   C   Y   T
118   agc atc aac acc act tgg tgt gct ggc tac tgc tac acc   156

R   D   L   V   Y   K   D   P   A   R   P   K   I
157   agg gat ctg gtg tat aag gac cca gcc agg ccc aaa atc   195

Q   K   T   C   T   F   K   E   L   V   Y   E   T
196   cag aaa aca tgt acc ttc aag gaa ctg gta tat gaa aca   234

V   R   V   P   G   C   A   H   H   A   D   S   L
235   gtg aga gtg ccc ggc tgt gct cac cat gca gat tcc ttg   273

Y   T   Y   P   V   A   T   Q   C   H   C   G   K
274   tat aca tac cca gtg gcc acc cag tgt cac tgt ggc aag   312

C   D   S   D   S   T   D   C   T   V   R   G   L
313   tgt gac agc gac agc act gat tgt act gtg cga ggc ctg   351

G   P   S   Y   C   S   F   G   E   M   K   E   *
352   ggg ccc agc tac tgc tcc ttt ggt gaa atg aaa gaa taa   390

```
      M   D   Y   Y   R   K   Y   A   A   I   F   L   V
  1  atg gat tac tac aga aaa tat gca gct atc ttt ctg gtc   39

T   L   S   V   F   L   H   V   L   H   S   A   P
 40  aca ttg tcg gtg ttt ctg cat gtt ctc cat tcc gct cct   78

D   V   Q   D   C   P   E   C   T   L   Q   E   N
 79  gat gtg cag gat tgc cca gaa tgc acg cta cag gaa aac  117

P   F   F   S   Q   P   G   A   P   I   L   Q   C
118  cca ttc ttc tcc cag ccg ggt gcc cca ata ctt cag tgc  156

M   G   C   C   F   S   R   A   Y   P   T   P   L
157  atg ggc tgc tgc ttc tct aga gca tat ccc act cca cta  195

R   S   K   K   T   M   L   V   Q   K   N   V   T
196  agg tcc aag aag acg atg ttg gtc caa aag aac gtc acc  234

S   E   S   T   C   C   V   A   K   S   Y   N   R
235  tca gag tcc act tgc tgt gta gct aaa tca tat aac agg  273

V   T   V   M   G   G   F   K   V   E   N   H   T
274  gtc aca gta atg ggg ggt ttc aaa gtg gag aac cac acg  312

A   C   H   C   S   T   C   Y   Y   H   K   S   *
313  gcg tgc cac tgc agt act tgt tat tat cac aaa tct taa  351
```

Figure 20
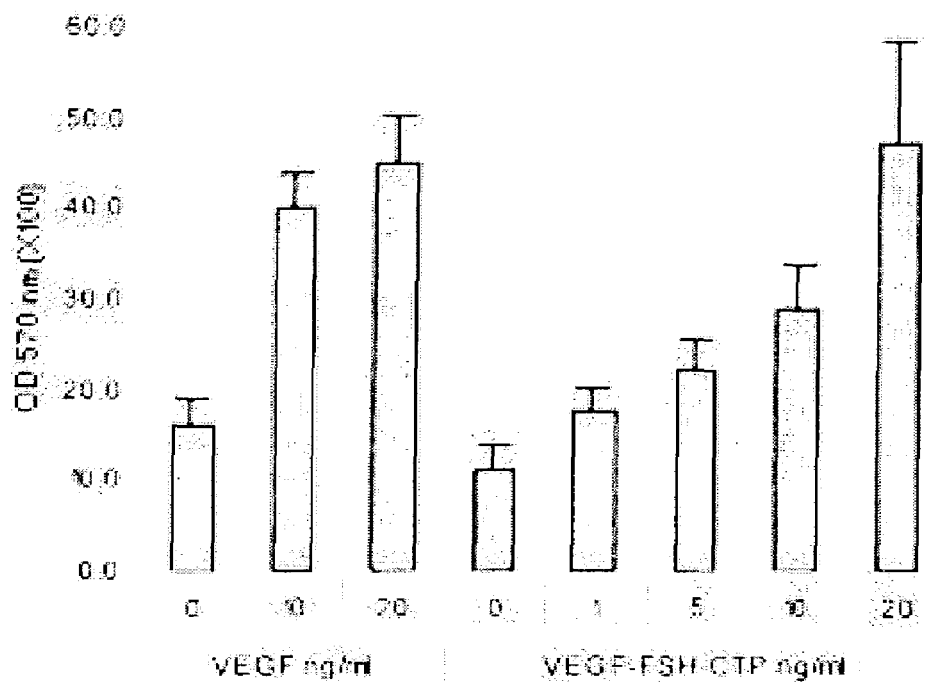
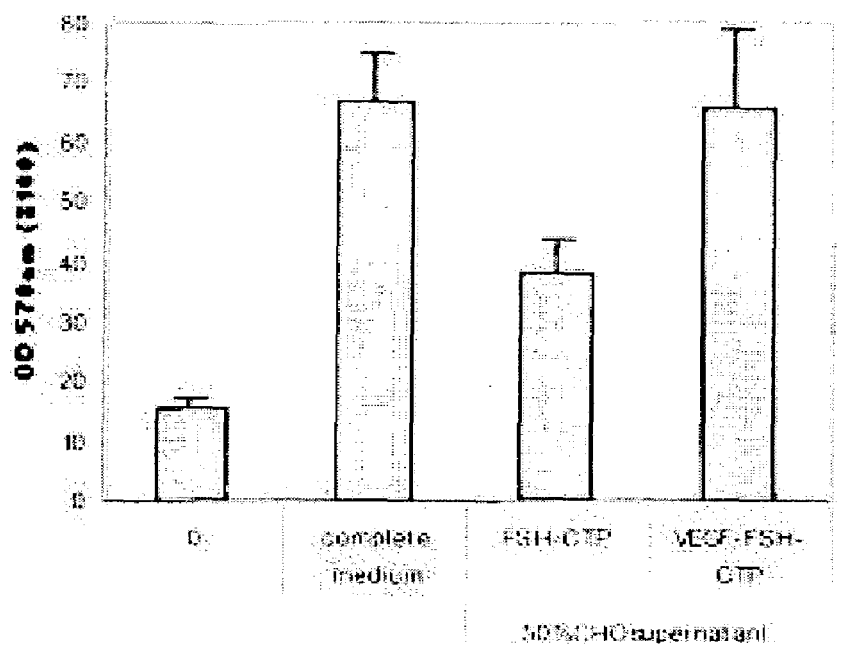

# LONG-ACTING HORMONE AND GROWTH FACTOR COMPOSITIONS AND USES THEREOF

This application is a continuation-in-part of U.S. Ser. No. 10/119,427, filed Apr. 9, 2002, now U.S. Pat. No. 7,173,113 B2, issued Feb. 6, 2007, which is a continuation-in-part of U.S. Ser. No. 10/062,931, filed Jan. 31, 2002, now abandoned, the contents of each of which are hereby incorporated into this application by reference.

Throughout this application, various publications are referenced by author and publication date. Full citations for these publications may be found at the end of the specification immediately preceding the claims. The disclosure of these publications is hereby incorporated by reference into this application to describe more fully the art to which this invention pertains.

The invention described herein was made with government support under grant number DK-51266 from the National Institutes of Health. Accordingly, the United States government has certain rights in this invention.

BACKGROUND OF THE INVENTION

One impediment to gonadotropin hormone replacement therapy has been the need for frequent repeated injections in order to maintain efficacious serum levels of the hormone. For example, current pharmacological formulations of follicle stimulating hormone (FSH) must be administered daily, often for 8 to 12 days when used to induce ovulation (LeContonnec et al, 1994). This dosing regimen is required due to the relatively short serum half-life of FSH. Thus, the development of more stable, longer-acting FSH formulations Glycoprotein hormones, including FSH, luteinizing hormone (LH), thyrotropin stimulating hormone (TSH) and chorionic gonadotropin (CG), are heterodimers comprised of two non-covalently bound subunits, α and β (Pierce et al, 1981). While the α-subunit is interchangeable among the hormones of this family, the β-subunit is unique and primarily responsible for the biological specificity of hormone action (see FIGS. 17 and 18 for the sequences of the hFSH β and α subunits, respectively).

The β subunits of hCG and hLH share greater than 85% sequence identity through the N-terminal 112 amino acids (Pierce et al, 1981). In addition, these two hormones share a common receptor and elicit similar biological activity following receptor binding. However, the serum half-life of hCG is almost five times that of hLH (Porchet et al, 1995; Saal et al, 1991; Yen et al, 1968). The main structural difference between β-hCG and β-hLH is an additional carboxy terminal peptide sequence on the β-hCG subunit, corresponding to amino acids 113-145 (Matzuk et al, 1990). This carboxy-terminal peptide, or "CTP", is now known to be the key determinant of the decreased metabolism and excretion of hCG, and thus of its long serum half-life, the longest among the glycoprotein hormones. The biological role of the carboxy-terminal extension of hCG is discussed in Matzuk et al, (1990). Surprisingly, the sequence of the CTP peptide itself is not responsible for the stability of this protein. Rather, it is the presence of four O-linked sugars that confer its remarkable stability. The characterization of the O-glycosylation sites of the hCG β subunit is described in Sugahara et al, (1996).

Many integral membrane proteins and secretory proteins are glycosylated. The most common type of glycosylation, called "N-linked", occurs when a sugar moiety is linked to the amide nitrogen of an asparagine residue within the consensus sequence Asn-X-Ser or Asn-X-Thr. The carbohydrate moieties of the gonadotropin hormones play an important role in the hormone's functionality. For example, appropriate glycosylation is required for protein folding and hormonal signal transduction. The importance of the asparagine-linked oligosaccharides of the hCG β subunit in correct disulfide bond pairing and thus on assembly and secretion are discussed in Feng et al, (1995) and Matzuk et al, (1990).

The O-linked glycosylations of the CTP sequence of hCG are so-named because the sugar moiety is linked to the hydroxyl group of either serine or threonine. This kind of linkage is much less common and, in contrast to N-linked moieties, O-linked sugars are not required for the hormonal activity of hCG. Schematic examples of N-linked and O-linked carbohydrates are shown in FIG. 14.

The importance of the CTP in promoting hormone stability was demonstrated by the construction of a fusion protein consisting of the CTP portion of the β-subunit of hCG and the carboxy terminus of β-hFSH (Fares et al, 1992). This β-hFSH-CTP fusion produced a long-acting hFSH agonist which was able to dimerize with a coexpressed α-subunit to produce a functional FSH hormone. Importantly, this β-hFSH-CTP demonstrated similar in vitro bioactivity and substantially increased in viva bioactivity compared with preparations of native hFSH.

Thus, merely adding the CTP sequence to β-hFSH was sufficient to increase the biological activity of the hormone, most likely through an increase in serum-half life. Indeed, recent pharmacokinetic parameter estimates in humans have demonstrated that this β-hFSH-CTP analog has an elimination half-life 2 to 3 times longer than that of native recombinant hFSH (Bouloux et al, 2001).

While the administration of pharmacological preparations of hFSH alone has been used in the treatment of infertility, this approach is likely to be enhanced substantially by methodologies which simultaneously induce follicular vascularization.

The primary mediator of follicular vascularization is VEGF, which is induced in response to FSH stimulation (Dissen et al, 1994). Reproductive aging is associated with diminished follicular vascularity, resulting somewhat paradoxically in an increase of VEGF, presumably in response to local hypoxia (van Blerkom et al, 1997). However, this adaptive response is often inadequate to reestablish appropriate vascular supply to the area.

Notably, improved vascularization has clinically been associated with improved oocyte yield, embryo morphology and pregnancy rates (Chui et al, 1997; Nargund et al, 1996). This is because perifollicular blood vessel development is critical to the health and integrity of the growing follicle.

Pharmacologic doses of exogenous VEGF can significantly ameliorate perifollicular hypoxia and improve follicular development in some patients. However, attempts to provide exogenous VEGF have suffered from severe side effects associated with the systemic administration of this growth factor.

SUMMARY OF THE INVENTION

This invention provides a first composition of matter comprising at least one subunit of a hormone or growth factor and a half-life increasing moiety, wherein the hormone or growth factor subunit and the half-life increasing moiety are covalently bound.

This invention also provides a second composition of matter comprising at least one subunit of a hormone or growth factor, a half-life increasing moiety, and a moiety that specifically binds to cells of a predetermined tissue.

This invention also provides a third composition of matter comprising at least one subunit of a hormone or growth factor, a β-FSH subunit, an α-FSH subunit and a half-life increasing moiety, wherein the hormone or growth factor, the β-FSH subunit, the α-FSH subunit and the half-life increasing moiety are covalently bound.

This invention also provides a pharmaceutical composition comprising any one of the instant compositions of matter and a pharmaceutically acceptable carrier.

This invention provides nucleic acids encoding the instant synthetic polypeptides, as well as expression vectors and suitable host cells for expressing same.

This invention also provides a method for producing the polypeptides of the instant invention that comprises growing a suitable host cell transfected with a vector encoding the polypeptide under conditions permitting its expression and recovering the polypeptide so expressed.

This invention also provides a method for increasing a subject's fertility which comprises administering to the subject an amount of the third instant composition effective to enhance the subject's fertility.

This invention also provides a method for increasing a subject's egg production which comprises administering to the subject an amount of the third instant composition effective to enhance the subject's egg production.

This invention also provides a method for increasing spermatogenesis in a subject through administering to the subject an amount of the third instant composition effective to enhance the subject's spermatogenesis.

This invention also provides a method for increasing vascularization in a tissue by contacting the tissue with an amount of a composition of the instant invention effective to increase vascularization in the tissue.

Finally, this invention provides a method for increasing the vascularization in ovarian tissue comprising contacting the tissue with an amount of the first instant composition, comprising VEGF, effective to increase vascularization in the ovarian tissue.

BRIEF DESCRIPTION OF THE FIGURES

FIG. 1: Nucleotide and predicted amino acid sequence of the fusion protein β-hFSH-N2 (SEQ ID NO:1) The N2 sequence is amino acids 130 through 146.

FIG. 2: Nucleotide and predicted amino acid sequence of the fusion protein β-hFSH-N4 (SEQ ID NO:2) The N4 sequence is amino acids 130 through 161.

FIG. 3: Nucleotide and predicted amino acid sequence of the fusion protein β-hFSH-CTP-α-hFSH (SEQ ID NO:3).

FIG. 4: Nucleotide and predicted amino acid sequence of the fusion protein β-hFSH-N2-α-hFSH (SEQ ID NO:4).

FIG. 5: Nucleotide and predicted amino acid sequence of the fusion protein β-hFSH-N4-α-hFSH (SEQ ID NO:5).

FIG. 12: Amino acid sequence of β-hCG (SEQ ID NO:6), wherein CHO is a glycosylation site and the black shading corresponds to the CTP. N-linked glycosylation is present on Asn, and O-linked glycosylation is present on Ser.

FIG. 15: Nucleotide and amino acid sequence of β-hFSH (SEQ ID NO:7). The signal sequence corresponds to the sequence beginning with the methionine at position 1 and ending with the cysteine at position 18.

FIG. 16: Nucleotide and amino acid sequence of α-hFSH (SEQ ID NO:8). The signal sequence corresponds to the sequence beginning with the methionine at position 1 and ending with the serine at position 24.

FIG. 20: Effect of VEGF-FSH on endothelial cell proliferation as determined by MTT assay. Panel A, native VEGF or VEGF-FSH was added to the medium at the indicated concentration. Panel B, cells were incubated with either EBM media, or a 1:1 mixture of EBM media and CHO cell supernatant taken from cells secreting either synthetic FSH-CTP or VEGF-FSH, as indicated.

DETAILED DESCRIPTION OF THE INVENTION

Definitions

Figure 6:
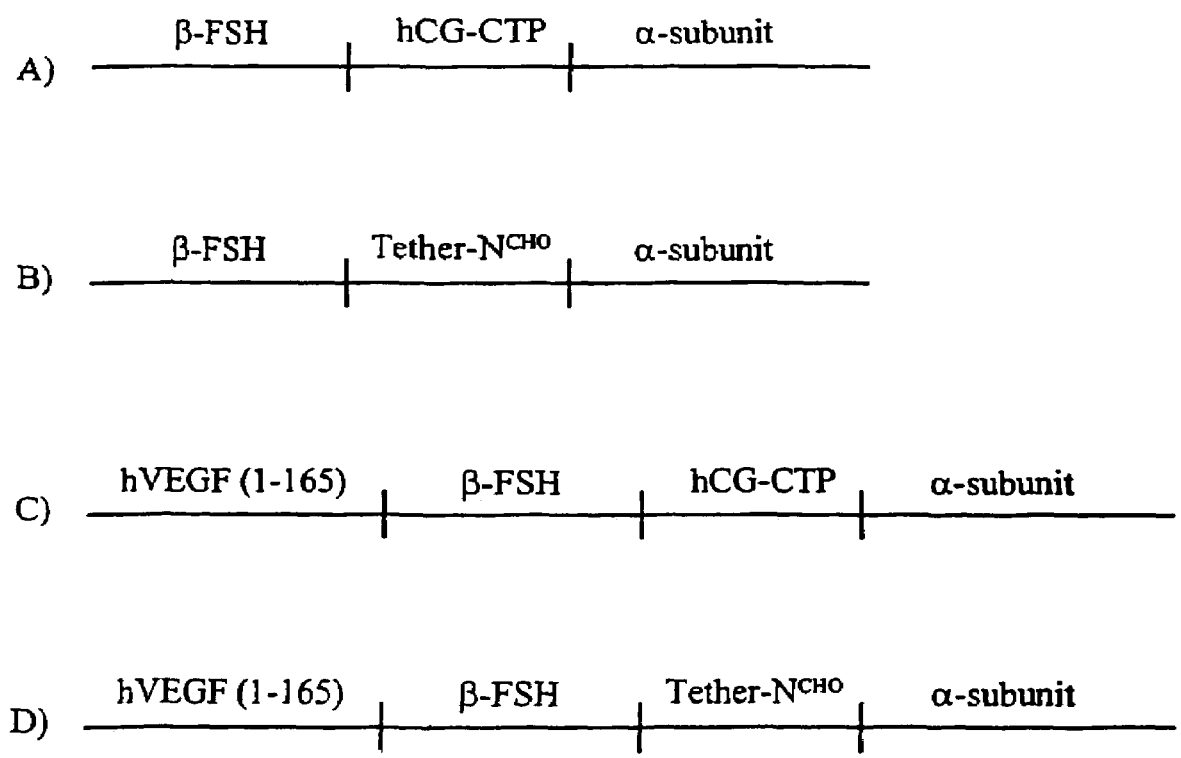
FIG. 6: (Panel A) Schematic β-hFSH-CTP-α construct; (Panel B) Schematic β-hFSH-N2/N4-α construct; (Panel C) Schematic VEGF-FSH-CTP construct; (Panel D) Schematic VEGF-FSH-N2/N4 construct.
Figure 7:
FIG. 7: Schematic of β-hFSH-CTP-α-hFSH construct with locations of restriction sites.

The terms "amino acid," "amino acid residue" or "residue" are used interchangeably herein to refer to an amino acid that is incorporated into a protein, polypeptide or peptide. The amino acid can be, for example, a naturally occurring amino acid or an analog of a natural amino acid that can function in a similar manner as the naturally occurring amino acid.

As used herein, "CTP" means the carboxy-terminal peptide of β-hCG, corresponding to amino acid residues 113-145. This portion of hCG contains multiple O-linked glycosylation sites (see FIG. 12).

The letter "h" is used herein to designate the human isoform of a protein or polypeptide. For example, hFSH means human follicle stimulating hormone. FSH is a pituitary glycoprotein essential for follicular growth as well as spermatogenesis, comprised of a noncovalently linked heterodimer of two peptide subunits, α and β. The β subunit is specific to FSH and thus determines its biological activity, while the α subunit is common to the other members of this glycoprotein family, for example, luteinizing hormone (LH), chorionic gonadotrophin (CG) and thyroid-stimulating hormone (TSH).

The terms "nucleic acid", "polynucleotide" and "nucleic acid sequence" are used interchangeably herein, and each refers to a polymer of deoxyribonucleotides and/or ribonucleotides. The deoxyribonucleotides and ribonucleotides can be naturally occurring or synthetic analogues thereof.

The terms "polypeptide," "peptide" and "protein" are used interchangeably herein, and each means a polymer of amino acid residues. The amino acid residues can be naturally occurring or chemical analogues thereof. Polypeptides, peptides and proteins can also include modifications such as glycosylation, lipid attachment, sulfation, hydroxylation, and ADP-ribosylation.

As used herein, "serum half-life", abbreviated "$t_{1/2}$", means elimination half-life, i.e., the time at which the serum concentration of an agent has reached one-half its initial or maximum value. The term "increased serum half-life" used herein in reference to a synthetic agent means that the synthetic agent is cleared at a slower rate than either the non-synthetic, endogenous agent or the recombinantly produced version thereof. For example, the $t_{1/2}$ of a synthetic FSH, e.g., hFSH-N2, in a subject would be "increased" if it exceeds the $t_{1/2}$ of either endogenous FSH or recombinantly produced native FSH.

As used herein, a "signal sequence" is an N-terminal portion of the nascent polypeptide chain that directs the polypeptide to the export apparatus of the cell and is itself cleaved from the nascent polypeptide, in general before posttranslational modification and secretion of the mature protein. The signal sequences and associated DNA region encoding these peptides for the beta and alpha hFSH chains are shown in FIGS. 15 and 16, respectively.

As used herein, "suitable host cells" include, but are not limited to, bacterial cells, yeast cells, fungal cells, insect cells, and mammalian cells. Mammalian cells can be transfected by methods well-known in the art such as calcium phosphate precipitation, electroporation and microinjection.

As used herein, "vector" means any nucleic acid vector known in the art. Such vectors include, but are not limited to, plasmid vectors, cosmid vectors, and bacteriophage vectors.

Units, prefixes and symbols may be denoted in their SI accepted form. Unless otherwise indicated, nucleic acid sequences are written left to right in 5' to 3' orientation and amino acid sequences are written left to right in amino- to carboxy-terminal orientation. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

In this invention, administering the instant pharmaceutical composition can be effected or performed using any of the various methods and delivery systems known to those skilled in the art. The administering can be performed, for example, intravenously, orally, via implant, transmucosally, transdermally, intramuscularly, and subcutaneously. In addition, the instant pharmaceutical compositions ideally contain one or more routinely used pharmaceutically acceptable carriers. Such carriers are well known to those skilled in the art. The following delivery systems, which employ a number of routinely used carriers, are only representative of the many embodiments envisioned for administering the instant composition.

Injectable drug delivery systems include solutions, suspensions, gels, microspheres and polymeric injectables, and can comprise excipients such as solubility-altering agents (e.g., ethanol, propylene glycol and sucrose) and polymers (e.g., polycaprylactones and PLGA's). Implantable systems include rods and discs, and can contain excipients such as PLGA and polycaprylactone.

Oral delivery systems include tablets and capsules. These can contain excipients such as binders (e.g., hydroxypropylmethylcellulose, polyvinyl pyrilodone, other cellulosic materials and starch), diluents (e.g., lactose and other sugars, starch, dicalcium phosphate and cellulosic materials), disintegrating agents (e.g., starch polymers and cellulosic materials) and lubricating agents (e.g., stearates and talc).

Transmucosal delivery systems include patches, tablets, suppositories, pessaries, gels and creams, and can contain excipients such as solubilizers and enhancers (e.g., propylene glycol, bile salts and amino acids), and other vehicles (e.g., polyethylene glycol, fatty acid esters and derivatives, and hydrophilic polymers such as hydroxypropylmethylcellulose and hyaluronic acid).

Dermal delivery systems include, for example, aqueous and nonaqueous gels, creams, multiple emulsions, microemulsions, liposomes, ointments, aqueous and nonaqueous solutions, lotions, aerosols, hydrocarbon bases and powders, and can contain excipients such as solubilizers, permeation enhancers (e.g., fatty acids, fatty acid esters, fatty alcohols and amino acids), and hydrophilic polymers (e.g., polycarbophil and polyvinylpyrolidone).

Solutions, suspensions and powders for reconstitutable delivery systems include vehicles such as suspending agents (e.g., gums, zanthans, cellulosics and sugars), humectants (e.g., sorbitol), solubilizers (e.g., ethanol, water, PEG and propylene glycol), surfactants (e.g., sodium lauryl sulfate, Spans, Tweens, and cetyl pyridine), preservatives and antioxidants (e.g., parabens, vitamins E and C, and ascorbic acid), anti-caking agents, coating agents, and chelating agents (e.g., EDTA).

Embodiments of the Invention

This invention provides a composition of matter comprising at least one subunit of a hormone or growth factor and a half-life increasing moiety, wherein the hormone or growth factor subunit and the half-life increasing moiety are covalently bound.

Half-life increasing moieties include, for example, a peptide containing one or more glycosylation sites. A half-life increasing moiety can also be nonpeptidyl, either in whole or in part, for example, polyethylene glycol.

In certain embodiments of the instant compositions of matter, the glycosylation is either O-linked or N-linked glycosylation. The number of glycosylation sites may be any number, such as one, two, three, four, five, or six sites. In a preferred embodiment, each site is separated from its adjacent site by about six amino acid residues.

In a preferred embodiment of the instant invention, the hormone or growth factor subunit and the polypeptide segment exist within a single polypeptide chain.

In an embodiment of any of the instant compositions of matter, the hormone or growth factor is selected from the group consisting of VEGF, GH, TGFα, TGFβ1, EGF, FGF, SCF, IGF-I, IGF-II, GDF-9, KGF, BMP-15, GM-CSF, LIF, follistatin, activin-β, a neurotropin, cadherin, angiopoiten I or II, MCP-1, ICAM-1, CD18, P-selectin and MIP-2. In a preferred embodiment, the growth factor is VEGF.

In an embodiment of any of the instant compositions of matter, the hormone or growth factor is from an animal selected from the group consisting of a primate, a horse, a sheep, a bird, a bovine, a pig, a dog, a cat and a rodent. In a preferred embodiment, the hormone or growth factor subunit is from a human.

In one embodiment of the first composition, the hormone or growth factor subunit is bound at its C-terminal end to the N-terminal end of the polypeptide segment. In another embodiment, the hormone or growth factor is bound at its N-terminal end to the C-terminal end of the polypeptide segment.

In yet a further embodiment of the first composition, the polypeptide segment comprises the carboxy-terminal portion of the β-hCG subunit. In the preferred embodiment, the carboxy-terminal subunit comprises the amino acid sequence corresponding to positions 113-145 of the β-hCG subunit.

The carboxy-terminal portion of the β-hCG subunit is preferably glycosylated on one or more serine residues, constituting one or more O-linked glycosylation sites. This polypeptide segment can also comprise a region having one or more N-linked glycosylation sites.

As used herein, an "N-linked" glycosylation site includes, without limitation, asn followed by any of X-ser, X-thr and X-cys, wherein X is any amino acid except proline, and glycosylation occurs on the asn residue. In this invention, the amino acid sequence of any polypeptide situated N-terminal to, C-terminal to, or in between two N-linked sites, can be of any content and length needed to suit a particular design requirement.

In another embodiment of the first composition, the polypeptide segment comprises the amino acid sequence ser-gly-ser-asn-ala-thr-gly-ser-gly-ser-asn-ala-thr-ser-gly-ser (SEQ ID NO:9).

In an embodiment of any of the instant compositions of matter, wherein the halflife increasing moiety is a polypeptide segment having the amino acid sequence ser-gly-ser-asn-ala-thr-gly-ser-gly-ser-asn-ala-thr-ser-gly-ser (SEQ ID NO:9), the polypeptide segment comprises one or a plurality of the amino acid sequence.

This invention also provides a second composition of matter comprising at least one subunit of a hormone or growth factor, a half-life increasing moiety, and a moiety that specifically binds to cells of a predetermined tissue.

This invention further provides a novel fusion protein incorporating VEGF, FSH and a half-life increasing moiety. The FSH moiety serves both to target the fusion protein to the ovaries and as a stimulus to follicular maturation. Importantly, both the VEGF and FSH thus targeted to the ovaries are biologically active as demonstrated by increased follicular vascularization and maturation. Thus, the present invention provides a significant development in the field of gonadotropin hormone replacement therapy.

Specifically, this invention provides a third composition of matter comprising at least one subunit of a hormone or growth factor, a β-FSH subunit, an α-FSH subunit and a half-life increasing moiety, wherein the hormone or growth factor, the β-FSH subunit, the α-FSH subunit and the half-life increasing moiety are covalently bound.

In one embodiment of the third composition, the growth factor is VEGF. In a further embodiment the α-FSH and β-FSH subunits are from an animal selected from the group consisting of a primate, a horse, a sheep, a bird, a bovine, a pig, a dog, a cat and a rodent.

In a preferred embodiment of the third composition, the α-FSH and β-FSH subunits are human α-FSH and β-FSH subunits which exist in a single chain polypeptide along with the VEGF and the half-life increasing moiety.

In a further embodiment of the third composition, the β-FSH subunit is bound at its C-terminal end to the N-terminal end of the polypeptide segment, and the polypeptide segment is bound at its C-terminal end to the N-terminal end of the α-FSH subunit. In this embodiment, the synthetic FSH comprises the N-terminal signal sequence of the β-FSH subunit.

In another embodiment of the third composition, the α-FSH subunit is bound at its C-terminal end to the N-terminal end of the polypeptide segment, and the polypeptide segment is bound at its C-terminal end to the N-terminal end of the β-FSH subunit.

In yet another embodiment of the third composition, the VEGF is bound at its C-terminal end to the β-FSH subunit, the β-FSH is bound at its C-terminal end to the N-terminal end of the polypeptide segment, and the C-terminal end of the polypeptide segment is bound to the N-terminal end of the α-FSH subunit.

This invention also provides a pharmaceutical composition comprising any one of the instant compositions of matter and a pharmaceutically acceptable carrier.

This invention provides nucleic acids encoding the instant synthetic molecules, as well as expression vectors and suitable host cells for expressing said molecules. Examples of vectors include a plasmid, a cosmid, λ phage and a yeast artificial chromosome, abbreviated "YAC". Any suitable cell system may be used to express the synthetic FSH molecules of the instant invention. For example, synthetic FSHs of the instant invention may be expressed in a bacterial cell or in a eukaryotic cell. In a preferred embodiment, a synthetic FSH is expressed in a Chinese hamster ovary cell, since this cell type provides certain advantageous post-translational protein modifications.

This invention also provides a method for producing a polypeptide that comprises growing a cell, for example a Chinese hamster ovary cell, under conditions permitting expression of the polypeptide encoded by the vector therein, and recovering the polypeptide so expressed. In a preferred embodiment, the vector encoding the polypeptide is transfected into the cells and subcultured under conditions that favor the growth of those cells which have taken up the vector. For example, the vector may contain one or more antibiotic resistance genes. Thus, medium containing the antibiotic will favor the growth of only those cells which have been transfected with the vector.

In a preferred embodiment, the polypeptide contains a signal sequence that targets the polypeptide for excretion from the cell. In a further embodiment, the excreted polypeptide may be collected, purified, and concentrated, for example by affinity chromatography, gel electrophoresis, and vacuum-assisted evaporation.

This invention also provides a method for increasing a subject's fertility which comprises administering to the subject an amount the third instant composition effective to enhance the subject's fertility. Determining a therapeutically effective amount of the instant composition can be done based on animal data using routine computational methods.

In one embodiment, this method is used to enhance the efficiency of in vitro fertilization protocols. For example, a composition of matter of the instant invention can enhance the success of in vitro fertilization by stimulating follicular maturation and egg production in the subject.

In a preferred embodiment of the instant invention, the composition is administered to the subject less frequently than current methods allow. For example, the instant composition may be administered every other day, every 6 to 8 days, or weekly. The instant composition can also be administered daily.

This invention also provides a method for increasing a subject's egg production which comprises administering to the subject an amount of the third instant composition effective to enhance the subject's egg production.

This invention further provides a method for increasing spermatogenesis in a subject through administering to the subject an amount of the third instant composition effective to enhance the subject's spermatogenesis.

This invention also provides a method for increasing vascularization in a tissue by contacting the tissue with an amount of a composition of the instant invention effective to increase vascularization in the tissue. The tissue may be, for example, heart, lung, vascular, testicular or dermal tissue. In a preferred embodiment, the tissue is ovarian tissue.

As used herein, a subject can be, for example, a primate, a horse, a sheep, a bird, a bovine, a pig, a dog, a cat, or a rodent. In the preferred embodiment, the subject is a human.

Finally, this invention provides a method for increasing the vascularization in ovarian tissue comprising contacting the tissue with an amount of the first instant composition, comprising VEGF, effective to increase vascularization in the ovarian tissue.

This invention is illustrated in the Experimental Details section which follows. This section is set forth to aid in an understanding of the invention but is not intended to, and should not be construed to, limit in any way the invention as set forth in the claims which follow thereafter.

Experimental Details

Methods

General

Cloning and preparation of plasmid DNA were performed with *E. coli* strain DH5α. Clones were grown in standard Luria-Bertani medium (LB) for purification of recombinant DNA constructs. Transformation of DH5α was performed according to standard techniques using calcium chloride.

PCR reactions were performed with Vent DNA polymerase (New England Biolabs, Beverly, Mass.) and all products of the reactions were sequenced to ensure that no mutations were introduced during the amplification.

Construction of the β-hFSH-CTP-α-hFSH Fusion Protein

An in-frame Xho I site was inserted adjacent to the initation codon of the β-hFSH cDNA sequence and a Bam HI site was inserted adjacent to the final codon, eliminating the terminator codon. Similarly, a Bam HI site was inserted adjacent to the codon for residue 113 in the cDNA encoding CTP and an Xba I site was inserted adjacent to the codon for residue 145. These two fragments were then ligated to form a contiguous Xho I-Bam HI-Xba I β-hFSH-CTP fusion lacking a terminator codon. This fusion was then ligated with a cDNA encoding the mature α-subunit which lacked the amino-terminal signal peptide but included the terminator codon, flanked by in-frame 5' Spe I and 3' Sac I sites. The final construct encodes a fusion of the β-hFSH and α-subunit with the CTP sequence as the linker sequence. This final fusion sequence was then inserted into an SV40 expression vector.

Construction of the β-hFSH-N2/N4-α-hFSH Fusion Protein

The β-hFSH-N2 and -N4 constructs consist of a single polypeptide chain hFSH molecule containing the β- and α-subunits tethered by a synthetic polypeptide consisting of either one or two tandem copies of the following: Ser-Gly-Ser-Asn-Ala-Thr-Gly-Ser-Gly-Ser-Asn-Ala-Thr-Ser-Gly-Ser. β-hFSH-N2 was constructed by synthesizing two complementary DNA strands encoding the above polypeptide in one of six potential reading frames. These two DNAs were designed such that following annealing a 5' Bam HI end and a 3' Spe I end were formed. The synthetic DNA duplex was then ligated into a vector with the hFSH β- and α-subunit encoding cDNAs. The in-frame ligation of these three DNAs was accomplished by placing a Xho I site immediately preceding the start codon and replacing the terminator codon of the hFSH β-subunit with a Bam HI site. In addition, an Spe I site was placed at the 5' end and a Sac I site immediately following the terminator codon of the α-subunit. The three fragments were then inserted into an SV40-based expression vector at Xho I/Sac I sites to form the β-hFSH-N2 expression construct. To insert a second copy of the synthetic polypeptide, a Bgl II site was inserted at the end of the synthetic sequence in the β-hFSH-N2 clone immediately preceding the Spe I site. The second copy of the synthetic polypeptide was then inserted by cleaving the β-hFSH-N2 construct with Bgl II and Spe I followed by insertion of the Bam HI/Spe I ended synthetic DNA to form β-hFSH-N4. This was feasible since Bam HI and Bgl II have identical cohesive termini.

Construction a VEGF-β-hFSH-CTP-α-hFSH (VEGF-FSH-CTP) Fusion

A 165-residue isoform of VEGF-A containing the heparin-binding domain was used herein. A cDNA encoding this isoform and its signal sequence but lacking the terminator codon was produced with an Xba I site at the 3' end. This cDNA was directly linked to an Xba I site placed at the 5' end of a single chain hFSH clone lacking the start codon and signal sequence, thereby fusing $VEGF^{165}$ to β-hFSH-CTP. The signal peptide on the $VEGF^{165}$ moiety was left unchanged for secreting the fused chimera. This particular orientation was chosen based on both crystallographic and growth factor activity analyses which suggested that the carboxy terminus of VEGF was more flexible and less directly involved in functional activities.

Construction a Long-acting VEGF Protein (VEGF-N2)

A long-acting VEGF protein was synthesized by tethering the $VEGF^{165}$ protein described above to a peptide having two tandem copies of the N-linked glycosylation signal sequence. The resulting fusion protein is designated VEGF-N2. As described above, the VEGF-N2 construct was transfected into CHO lines for protein production and purification. The synthetic protein was detected by immunoblotting with anti-VEGF antibodies.

Expression of Fusion Proteins

An SV40 expression clone containing the fusion construct was co-transfected into Chinese hamster ovary cells (CHO-K1) along with an SV2neo clone encoding resistance to the antibiotic G418. The CHO cell transformation was performed using a standard calcium phosphate precipitate technique. Media containing G418 (Gemini Bioproducts, Woodland, Calif.) was used to select transfected cells and media was assayed for secretion of the fusion protein using an hFSH-specific radioimmunoassay. Isolated colonies were pooled and maintained in Ham's F-12 culture medium containing 500 ug/mL G418, 10% fetal bovine serum, 100 units/mL penicillin, 100 ug/mL streptomycin, and 4 mM glutamine. Pooled colonies were subcloned in 96 well microtiter dishes and high-secreting clones were isolated. To further increase the yield of the secreted fusion proteins, the cells were grown in suspension cultures.

Purification of Fusion Proteins

Spinner bottles were seeded at $10^5$ cells/mL in CHO-S-SFM medium (Life technologies, Rockville, Md.) containing 400 ug/mL G418. Cultures generally reached a density of $2 \times 10^6$ cells/mL on day 6 or 7, and the cell supernatant was harvested on day 7 or 8. PMSF was added to the supernatant at a concentration of 0.2 mM, which was then filtered through a 0.2 μm membrane and stored at 4° C. Affinity purification of was accomplished using an A201 (α-subunit specific antibody column). The column was prepared by coupling purified A201 immunoglobulins to CNBr-Sepharose-4B according to the manufacturer's instructions (Amersham Pharmacia Biotech, Piscataway, N.J.) at a concentration of 5 mg antibody/mL Sepharose. After applying the cell supernatant, the column was washed with 50 bed volumes of PBS followed by 2 bed volumes of distilled water. The fusion protein was eluted with 3-4 bed volumes of 1 M acetic acid and immediately dried on a Speed-Vac concentrator (Savant Instruments, Holbrook, N.Y.).

Subcutaneous Protocol

Rhesus monkeys were injected subcutaneously with the fusion protein (n=4) or r-hFSH (Follistim, Organon Inc., n=2) at a dose of 10 IU/kg. All except 1 of the monkeys in each of the two treatment groups had been ovariectomized prior to injection. Serum hFSH was assayed prior to injection and at the following intervals post-injection: 12 h, 16 h, 20 h, 24 h, 36 h, 48 h, 60 h, and every 24 hours thereafter until levels reached baseline (approximately 9 days for control animals, 19-22 days for treatment animals).

Intravenous (IV) Protocol

One rhesus monkey was given an IV bolus of the fusion protein (10 IU/kg). A second animal was given an IV bolus of the control, r-hFSH at the same dose. Serum was assayed for hFSH prior to bolus administration and at the following intervals post-injection: 0.5 h, 1 h, 2 h, 4 h, 8 h, 12 h, 24 h, 36 h, 48 h, 72 h, 96 h, 120 h, 144 h and 168 h.

Pharmacokinetics

Recombinant human FSH (r-hFSH) (Follistim, Organon Inc, West Orange, N.J.) was used as a control. The Immulite assay (Diagnostic Products Corporation, Los Angeles, Calif.) was used to quantitate hFSH protein. This assay was able to detect the hFSH analogues in vitro and in vivo, and did not cross-react with rhesus FSH.

Pharmacokinetic Analysis

Each individual data set was evaluated by the pharmacokinetic data analysis program PKAnalyst (Micromath, Inc., Salt Lake City, Utah). For the IV dosing study, the following biexponential equation was fitted to the data: $C(t)=Ae-at+Be-bt$, where C(t) is the plasma concentration at time "t", and A and B are the multiexponential coefficients. Values of a and b represent the initial-phase disposition rate constant and the terminal-phase disposition rate constant, respectively. PKAnalyst was used to generate the best-fit critical pharmacokinetic parameters, including elimination rate constant, half-life of initial (distribution) phase ($t_{1/2a}$), half-life of terminal (elimination) phase ($t_{1/2b}$), and total area under the blood concentration-time curve (AUC).

For the subcutaneous dosing studies, the blood concentration-time data were represented by the following biexponential equation: $C(t)=A(e-Ket-e-Kat)$, where C(t) is the blood concentration at time "t" and A the multiexponential coefficient. Ke and Ka represent the elimination rate constant and absorption rate constant, respectively. All parameter estimates were computed by PKAnalyst. Bioavailability of r-hFSH and the hFSH analogues were estimated from the ratio of AUC (SC)/AUC (IV), at a constant dose (10 IU/kg).

In vivo FSH Bioactivity

Ganirelix Acetate (250 μg) was administered by SC injection for 10 consecutive days to two normally cycling Rhesus monkeys beginning menstrual cycle day 4. The hFSH analogue was administered as a single subcutaneous dose (10 IU/kg) on cycle day 6. Venipuncture was performed daily and serum assayed for estradiol levels from cycle day 2 through cycle day 14. Serum estradiol was measured using an automated Immulite assay (Diagnostic Products Corporation, Los Angeles, Calif.).

Alternatively, hypophysectomized mice (surgery at 19 days) were purchased from the Charles River Company (Wilmington, Mass.). Upon arrival, mice were rehydrated with glucose-supplemented water for four days and randomized into control and experimental groups. Control recombinant hFSH protein or hFSH analogue was administered via a single subcutaneous injection in a total volume of 100 microliters at a dose of 10 IU. On day four post-injection, the animals were weighed and sacrificed by carbon dioxide asphyxiation followed by cardiopuncture and drainage. The uterus and ovaries were weighed and sectioned for histologic analysis.

Carbohydrate Analysis

MALDI-TOF mass spectrometry combined with exoglycosidase digestion was used to determine the carbohydrate composition of the synthetic analogues described herein, using an adaptation of the technique described in Kim et al, 2001. Briefly, disulfide bond reduction is followed by a tryptic digest and/or other enzymatic digests to liberate peptides containing single carbohydrate side chains. The mass of each glycosylation variant is determined by calculating the difference in mass between the observed peptide and its nonglycosylated primary sequence. Further analysis may include N-linked profiling and sequencing, O-linked profiling and monosaccharide composition analysis using "FACE"™ technology kits from (Glyko, Novato, Calif.).

Ambiguities from the FACE™ analysis were resolved by a compositional analysis. Acid hydrolysis was followed by HPLC chromatography with a CARBOPAC™ PA1 anion exchange column (Dionex, Sunnyvale, Calif.). The carbohydrate content was quantitated by comparing peak areas to a standard mixture. For sialic acid analysis the conditions were appropriately modified. Additionally, techniques such as protein sequencing were used to determine if specific sites were glycosylated in synthetic sequences described herein. Both O-linked and N-linked glycosylated residues are "hidden" from this analysis due to the added carbohydrate. Therefore the "absence" of a serine residue, from a known sequence suggests the presence of a carbohydrate moiety at that position.

In vitro FSH Bioactivity

Bioactivity of the hFSH analogues was evaluated using Y-1 cells transfected with the FSH receptor. Y-1 cell cultures were mixed with the fusion protein and native pituitary hFSH (control) at varying concentrations and media was assayed for cAMP activity as described in Bouloux et al, 2001.

In vitro VEGF Bioactivity

Endothelial Cell Proliferation (metabolism): Human microvascular endothelial cells were used in a standard MTT assay (HMVEC-d Neo, Clonetics, San Diego, Calif.). Briefly, cells were seeded at 3000 cells per well in a 96 well plate in basal medium (EBM, Clonetics) containing 2% FBS, but devoid of growth factors. After a 2-day starvation period, the media was replaced with media containing either the fusion protein or native recombinant VEGF. Two days later this media was replaced with fresh media containing the same factors. Following another three days of culture, the number of actively metabolizing cells was determined using an MTT assay (R & D systems, Minneapolis, Minn.).

VEGF Receptor Activation: Microvascular endothelial cells isolated from human foreskin were plated at 100,000 cells per well in 12 well plates and cultured for 5 hr in EBM media containing growth factors and other nutrients. The cells were then starved overnight in EBM medium containing 0.2% BSA, with no other additives. Following starvation, approximately 0.5 pmol of either VEGF, the VEGF-FSH fusion protein or hFSH-CTP was added to the medium. After a 1 hr incubation at 4° C., the cells were washed twice in cold PBS containing calcium and magnesium then lysed in a standard RIPA buffer containing protease inhibitors (50 mM HEPES pH 7.2, 10 mM EDTA, 0.1%SDS, 1% NP-40, 0.5% deoxycholate, 50 mM Na-pyrophospate, 100 mM NaF, 2 mM orthovanadate pH 7.5, 1 mM zinc acetate and one protease inhibitor pill per 50 ml of solution (Roche, Indianapolis, Ind.)). The lysate was filtered by centrifugation in a 0.65 micron Durapor PVDF filter (Millipore, Bedford, Mass.) at 3,000 rpm for 30 min. The filtrate was incubated with 10 ug/ml anti-KDR antibody (monoclonal antibody 2-10-1) for 2 hr. Protein A-Sepharose (Amersham/Pharmacia Biotech, Piscataway, N.J.) was added and the mixture was incubated overnight at 4° C. with gentle mixing. The Sepharose was washed twice with RIPA buffer and then boiled for 5 min. in 25 ul 2×SDS-PAGE sample buffer. Supernatants were electrophoresed on a gradient gel of 4-15% acrylamide (BioRad, Hercules, Calif.) and electroblotted onto a PVDF membrane. After blocking, the membrane was washed 3×in PBS with 0.05% Tween 20 (PBS-T). The membrane was incubated overnight in horseradish peroxidase-conjugated anti-phosphotyrosine (10 ng/ml) monoclonal antibody (clone 4G10, Upstate Biotechnology, Lake Placid, N.Y.) in PBS-T containing 3% BSA. The membrane was washed 3× in PBS-T and developed using a chemiluminescent system (ECL, Arnersham Pharmacia Biotech, Piscataway, N.J.).

In vivo Bioactivitty

Hypophysectomized female mice (surgery at 19 days) were purchased from the Charles River Company (Wilmington, Mass.). Upon arrival, mice were rehydrated with glucose-supplemented water for 4 days, and subsequently randomized to one of the following groups (n=5 for each group) : (1) saline, (2) hFSH-CTP, (3) VEGF-FSH, or (4) co-administration of hFSH-CTP+dimeric VEGF. Hormone or control was administered by a single SC injection in a total volume of 100 uL at a dose of 10 IU (mice in group 4 received 10 IU of both hFSH analogue and dimeric VEGF). Mice were housed separately according to group, fed standard mouse feed, and given water supplemented with glucose throughout the study period. On day 4 post-injection, animals were weighed and sacrificed by carbon dioxide asphyxiation followed by cardiopuncture and drainage. The uterus and ovaries of each animal were extirpated, weighed, sectioned and stained with H & E.

Histologic Preparation and Follicle Counts

Both ovaries were removed from each animal. One ovary was weighed, immersed in formalin for fixation and embedded in paraffin according to standard protocols. Sections were cut at four to five micron intervals and every tenth section was stained with hematoxylin and eosin. Follicle density and maturation were assessed using the method of Pedersen and Peters (1968).

Perifollicular capillary density was assessed by counting the number of capillaries under 600× magnification in H & E stained sections, using an ocular containing a grid covering 25 um$^2$. Serial sections were counted, with the grid directed over the periphery of follicles (avoiding the avascular center of the follicle).

Immunostaining for PECAM and Blood Vessel Density Analysis

The contralateral ovary was embedded in OCT (Tissue-Tek, Torrance, Calif.), snap frozen in isopentane, and stored at −80° C. Frozen ovaries were sectioned at 5 micron intervals. Sections were dehydrated and permiablilzed in 24° C. acetone for 2 min and then rehydrated in phosphate-buffered saline (PBS) containing 1% hydrogen peroxide for 30 min followed by blocking with rabbit serum diluted 1:50 in PBS containing 3% BSA. A rat anti-PECAM antibody was used at a 1:1000 dilution (Vecchi et al, 1994), PharMingen, San Diego, Calif., followed by a biotinylated rabbit anti-rat IgG (Vector Laboratories, Burlingame, Calif.) used at a dilution of 1:2000 for 30 min at room temperature. Visualization of bound antibodies was achieved by incubation with avidin and horseradish-peroxidase-conjugated biotin in PBS (1:100 dilution) for 30 min (Vectastain Standard ABC Elite kit, Vector Laboratories). Peroxidase staining was performed with diaminobenzidine tetrahydrochloride (DAB) as achromogen (DAB Substrate kit, Vector Laboratories, Burlingame, Calif.). Tissues were counterstained with hematoxylin.

Blood Vessel Density: To determine blood vessel density, PECAM immunostained sections were examined using a 10×10 eyepiece grid under a 40× objective as previously described by Ferrara et al, (1992; 1998). Using this magnification, a grid covers a region of 0.063 mm$^2$. Random regions of the follicle perimeter were selected to fill the grid, avoiding the avascular interior of the follicles. Each square within a grid containing a PECAM-positive endothelial cell was counted as one "hit". Vascular density is expressed as the absolute number of "hits". An average number of hits from 5 independent, randomly selected ovarian sections from control and treatment animals was routinely used in these analyses.

Non-ovarian Tissue: Systemic effects of VEGF-FSH were evaluated using immunhistochemical detection of PECAM in snap frozen liver and kidney sections.

Inhibin Assay

Inhibin A, produced by developing follicles, provides an indirect measure of follicle number and maturity. Serum inhibin levels from mice and rats injected with the synthetic FSH analogues and control peptides or saline were determined using an enzyme-linked immunoassay specific for the inhibin A dimer (Oxford Bio-Innovation LTD, Oxfordshire, UK). This assay is able to detect rat and mouse inhibin A reproducibly.

Results

Example 1

The β-hFSH-CTP-α Fusion Protein

In vitro Bioactivity

Figure 8:
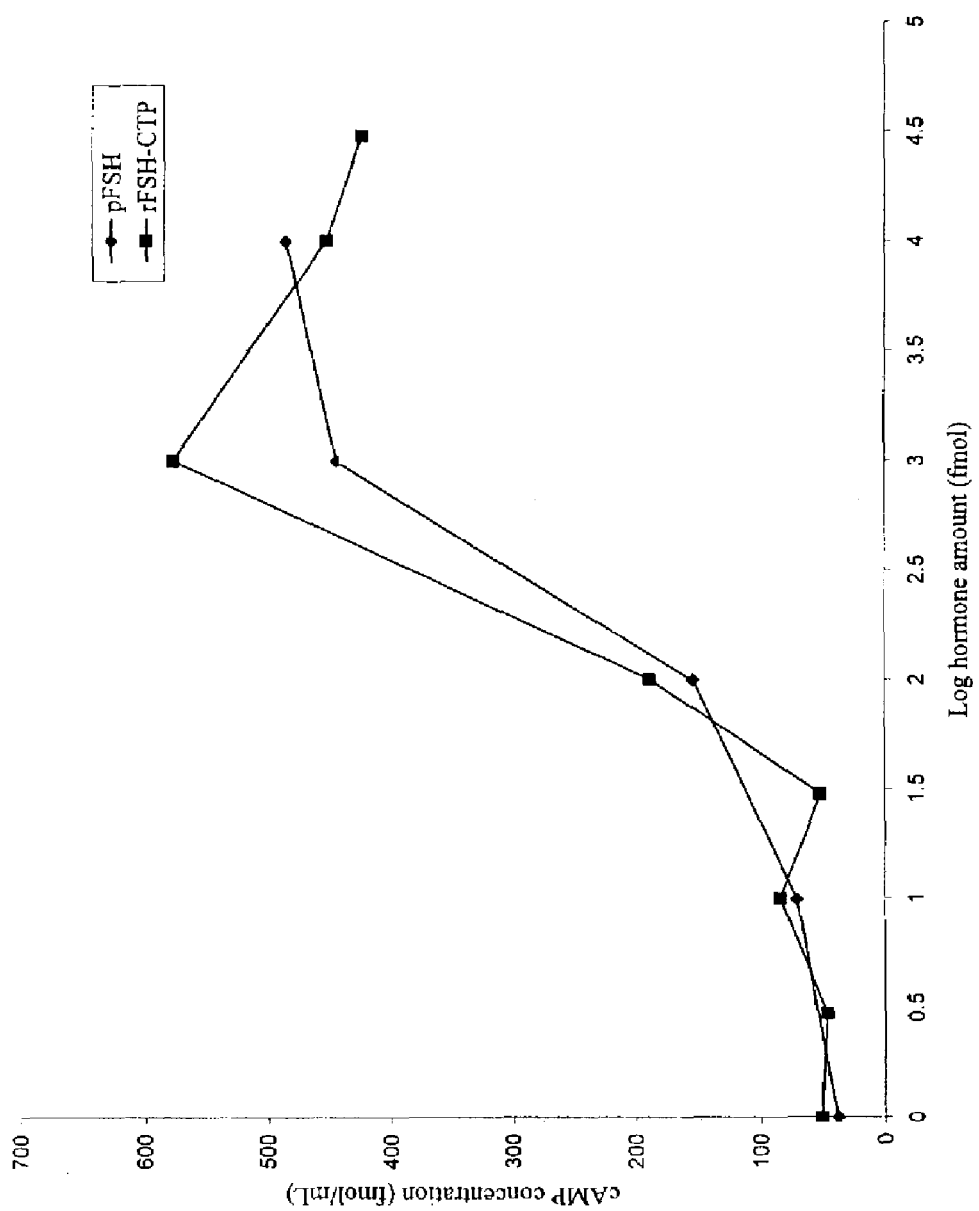
FIG. 8: In vitro bioassay of hormone activity. cAMP concentration (fmol/ml) was quantitated in Y1 cells expressing the FSH receptor after treatment with the indicated amount of either pituitary FSH (pFSH) or the FSH analogue, β-hFSH-CTP-α-hFSH (rFSH-CTP).

The bioactivity of the β-hFSH-CTP-α analogue was first assessed by an assay of hFSH receptor activity. In this assay, a recombinant native hFSH receptor is expressed in a suitable host cell and cAMP induction is measured following incubation with hormone (Lindau-Shepard et al, 2001). As shown in FIG. 8, the β-hFSH-CTP-α analogue induced a similar rise in cAMP levels when compared with recombinant hFSH, demonstrating that this single-chain fusion analogue folded properly into an unhindered, biologically active hormone.

Pharmacokinetics

In order to establish the pharmacokinetic parameters of the instant synthetic FSH, Rhesus monkeys were injected with an IV bolus dose (10 IU/kg) of either a recombinant native hFSH, or the β-hFSH-CTP-α analogue. The serum concentration of hFSH was determined by immunoassay at times following injection and a serum concentration-time curve was generated based on the data. For both the recombinant native hFSH and the β-hFSH-CTP-α analogue, the resulting curve fit a two-compartment model, consisting of an initial distribution half-life and a second, slower, elimination half-life. As indicated by the pharmacokinetic parameter estimates listed in Table 1, the half-life of elimination for the β-hFSH-CTP-α analogue was more than four-fold longer than that of the native hFSH.

TABLE 1

Pharmacokinetic parameter estimates after IV bolus injection of rhFSH-CTP or the control recombinant hFSH protein (rhFSH), each at a dose of 10 IU/kg.

| PARAMETER | rhFSH-CTP | rhFSH |
|---|---|---|
| $T_{1/2\ distribution}$ (hr) | 3.16 | 1.39 |
| $T_{1/2\ elimination}$ (hr) | 35.29 | 8.25 |
| AUC (mIU/ml d) | 278 | 38.8 |
| Clearance (1/kg hr) | 1.5 | 10.74 |

Figure 9:
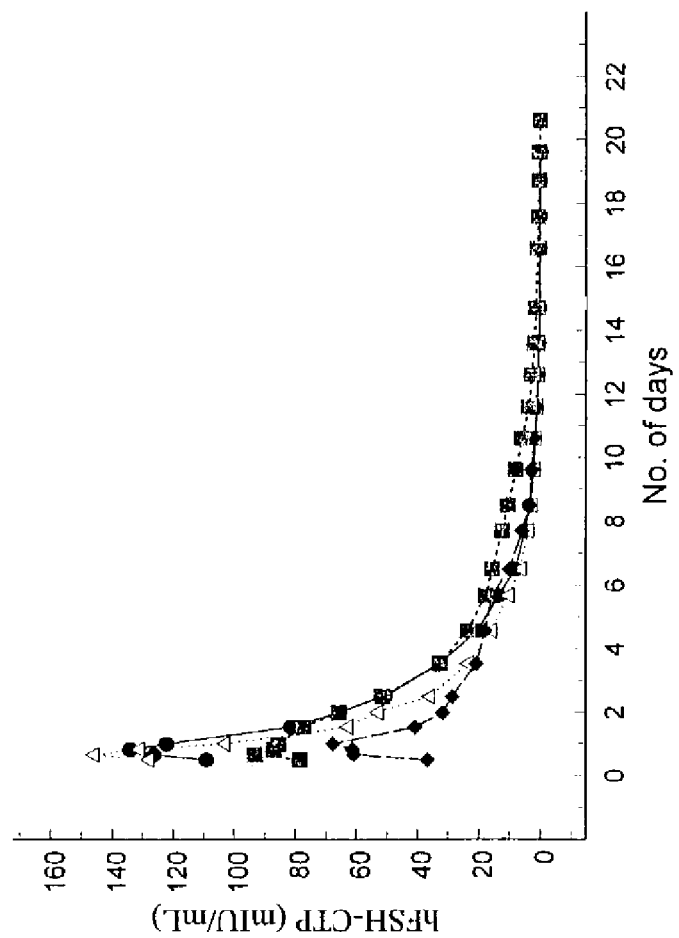
FIG. 9: Serum levels of the FSH analogue, β-hFSH-CTP-α-hFSH (hFSH-CTP), in 4 rhesus monkeys (indicated by triangles, inverted triangles, circles, and squares, respectively) measured at the indicated times following a single subcutaneous injection at a dose of 10 IU/kg.
Figure 10:
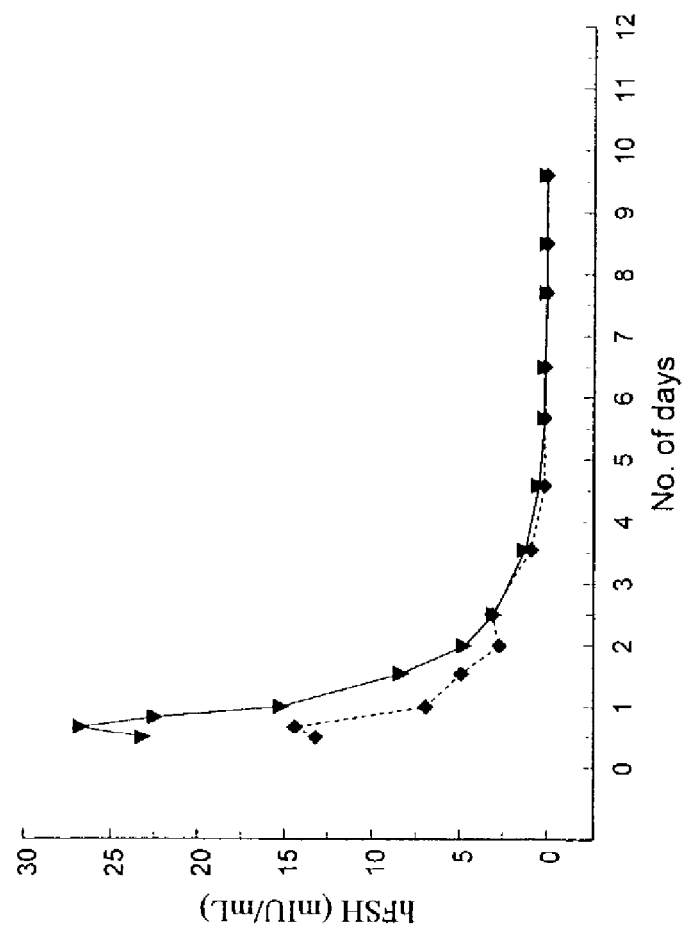
FIG. 10: Serum levels of the control recombinant hFSH protein, (hFSH), in 2 rhesus monkeys (indicated by diamonds and triangles, respectively) measured at the indicated times following a single subcutaneous injection at a dose of 10 IU/kg.

Although these results obtained following an intravenous bolus injection were encouraging, it was also important to determine the pharmacokinetic parameters of the synthetic FSH following a subcutaneous injection. This is because subcutaneous administration is a relatively easier route for clinical use. As indicated by the serum concentration-time curves for treatment animals (n=4) receiving the β-hFSH-CTP-α analogue (FIG. 9) and controls (n=2) receiving native hFSH (FIG. 10), the serum levels of native hFSH approached baseline by day 4 post-injection, whereas elevated (>2 mIU/mL) levels of the β-hFSH-CTP-α analogue were maintained for approximately 10 days. These data fit a one-compartment pharmacokinetic model, the parameter estimates of which are given in Table 2.

TABLE 2

Mean pharmacokinetic parameter estimates after subcutaneous injection of β-rhFSH-CTP (n = 4) or the control, rhFSH (n = 2), each at a dose of 10 IU/kg. Bioavailability was calculated as AUCsc/AUCiv.

| PARAMETER | rhFSH-CTP | rhFSH |
|---|---|---|
| $T_{1/2\ elimination}$ (hr) | 35.23 | 15.74 |
| $T_{1/2\ absorption}$ (hr) | 5.04 | 1.75 |
| $C_{max}$ (mIU/ml) | 101.26 | 25.77 |
| $T_{max}$ (hr) | 16.39 | 5.95 |
| AUC (mIU/ml d) | 275.31 | 30.96 |
| Bioavailability (%) | 99 | 80 |

Figure 13:
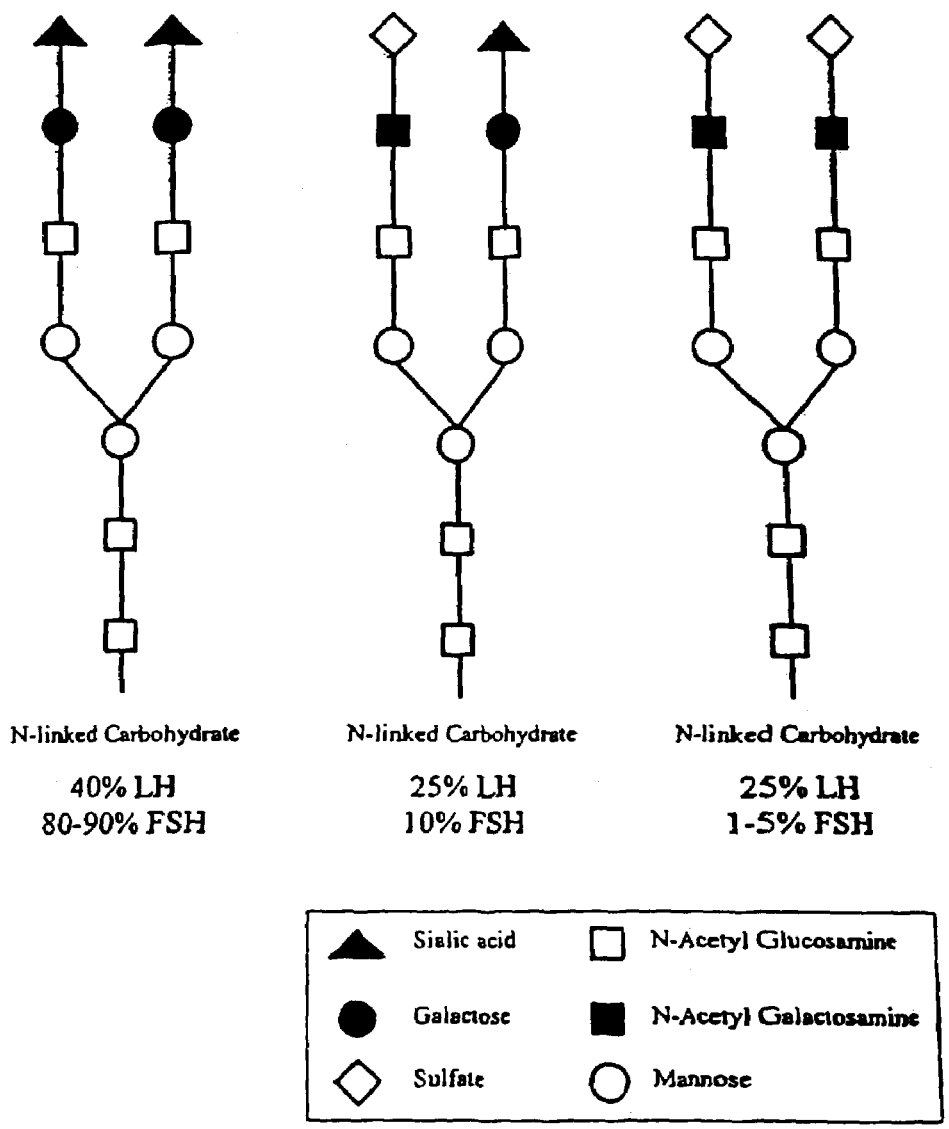
FIG. 13: Schematic of the carbohydrate moieties on both hLH and hFSH and some of the microheterogeneity which results in the wide range of isoelectric points in the glycoprotein hormones.
Figure 14:
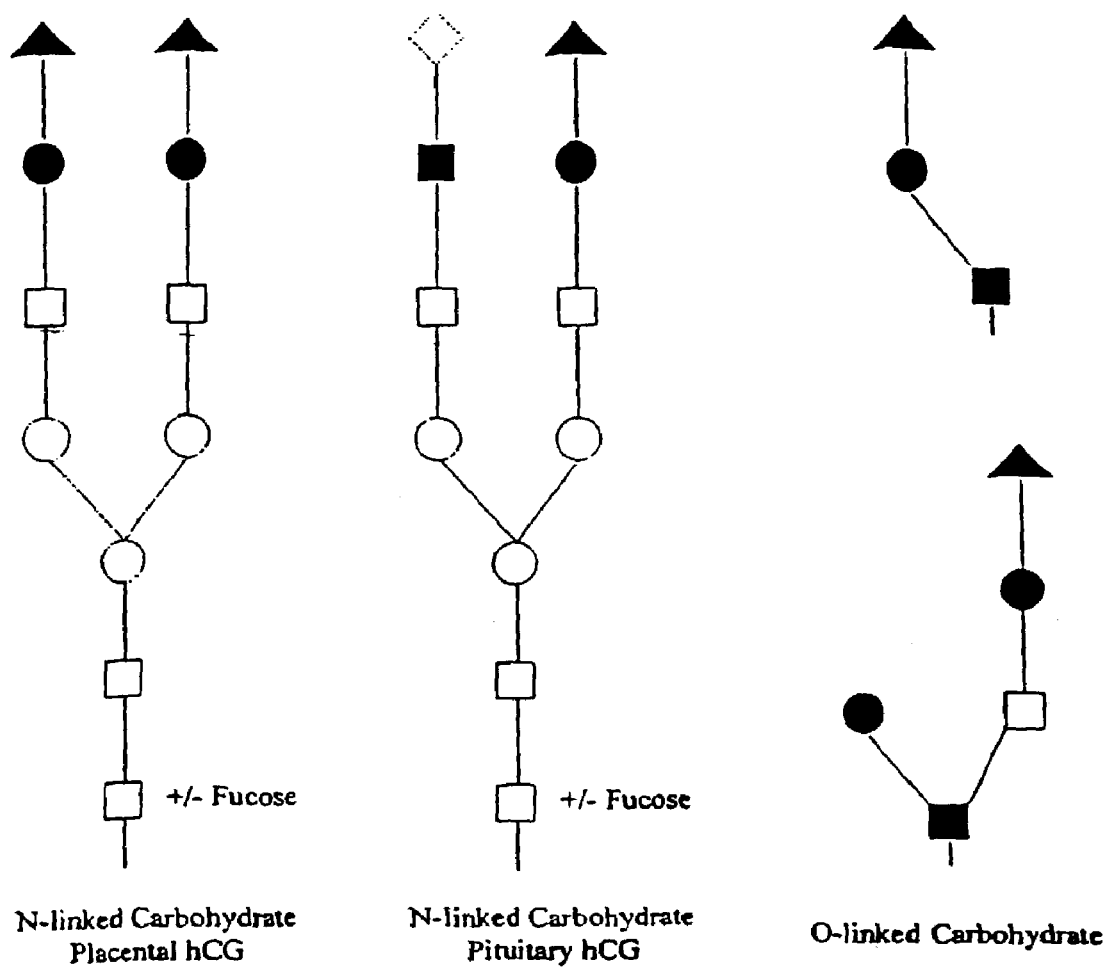
FIG. 14: Schematic examples of N-linked and O-linked carbohydrates.

Notably, the half-life of absorption for the instant synthetic FSH was approximately threefold longer than that of the native hFSH. These results show that the half-life of elimination correlates well with the intravenous data and confirms the slower metabolism and clearance of the β-hFSH-CTP-α analogue. Addition of the CTP moiety to hFSH thus induced a depot effect, retarding the absorption of the product following subcutaneous administration. This explains the slower time to reach peak concentration ($t_{max}$) for animals receiving the β-hFSH-CTP-α analogue. As indicated in FIG. 13, both drugs were highly bioavailable after subcutaneous administration.

In vivo Bioactivity

Figure 11:
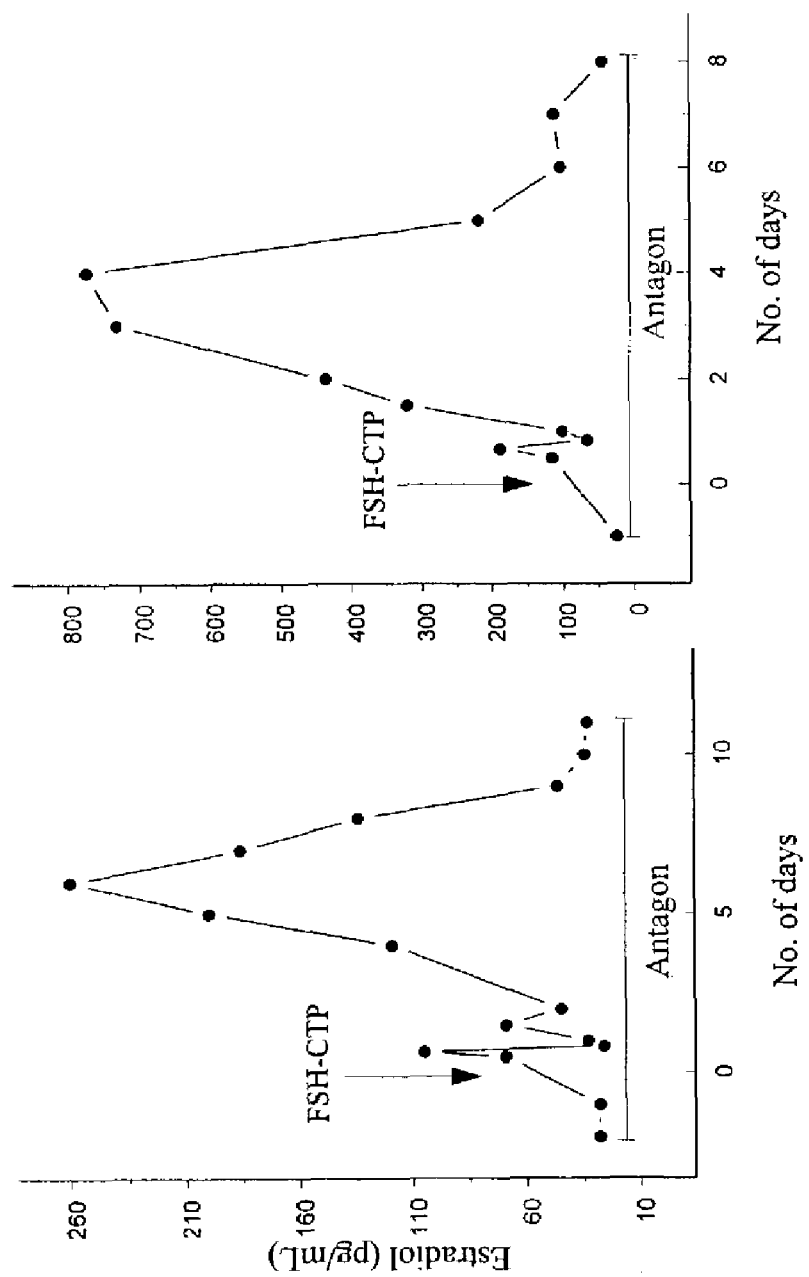
FIG. 11: Serum estradiol levels in two normally cycling monkeys following a single subcutaneous injection of the FSH analogue, β-hFSH-CTP-α-hFSH (FSH-CTP). The time of injection is indicated by arrows. Both monkeys were given the GnRH antagonist Ganirelix Acetate for the duration of the study.

To establish the bioactivity of the β-hFSH-CTP-α analogue in vivo, two normally cycling monkeys were injected with a single dose of the analogue, and serum was assayed for estradiol at various times following injection. Both monkeys were given a GnRH antagonist (Antagon, Organon, West Orange, N.J.) for the duration of the study, eliminating any effect on ovarian estrogen production from endogenous Rhesus FSH. As shown in FIG. 11, serum estradiol levels initially increased in both animals, with peak levels achieved at 3 and 5 days post-injection. One monkey attained supraphysiologic levels of estradiol (peak 773 pg/mL) on day 4 post-injection, suggesting early recruitment of multiple follicles. Thus, the β-hFSH-CTP-α analogue demonstrated similar, and in one case substantially increased, in vivo biological activity compared to native hFSH.

Conclusions

The results presented herein demonstrate that the addition of CTP to the carboxy terminus of the β subunit of hFSH had no adverse impact on folding of the molecule, receptor binding, or in vitro signal transduction. Furthermore, the fusion protein was metabolized at a slower rate than the native hormone, as circulating levels remained elevated for an extended period of time compared to native recombinant hFSH. Quantitatively, the half-life of elimination for the β-hFSH-CTP-α analogue following subcutaneous administration was 2 to 3 times longer than that of native recombinant hFSH. This difference corresponds well with the only previous report on pharmacokinetics in humans, which was done with male subjects, in which the half-life of elimination after subcutaneous administration was prolonged by a similar magnitude compared with historic controls receiving native hormone.

These results also confirm the accuracy of our parameter estimate for elimination half-life by assessing pharmacokinetics after IV administration. Surprisingly, absorption of the β-hFSH-CTP-α analogue was delayed by approximately three-fold following subcutaneous administration. The long circulating presence of the β-hFSH-CTP-α analogue after subcutaneous administration is thus explained not only by a decreased metabolism of the protein, but by a depot effect resulting in slower absorption.

In summary, the pharmacodynamics and biological activity of a β-hFSH-CTP-α analogue in a primate model are described herein for the first time. Administration of the β-hFSH-CTP-α analogue to 2 monkeys given a GnRH antagonist (to suppress endogenous FSH activity) elicited a dramatic rise in serum estradiol levels. A single subcutaneous dose resulted in elevated estradiol levels for 5-7 days, with one monkey achieving a peak estradiol level greater than 3 times that seen during a normal endogenous Rhesus cycle.

This supraphysiologic response is indicative of multifollicular recruitment, although sonographic confirmation was not performed. Such prolonged elevations in estradiol are not normally seen after isolated subcutaneous injections of native recombinant hFSH.

These results confirm the feasibility of achieving prolonged ovarian stimulation following a single injection of a recombinant gonadotropin analogue. Fewer injections will result in less patient discomfort, improved compliance, and possibly a reduction in the number of local side effects.

Combination therapy using both long and short-acting FSH formulations, either together and/or sequentially during a stimulation cycle, should also be considered. In these cases, the short-acting (native) formulation may be used to "fine-tune" the FSH dose after an initial bolus of a long-acting analog.

Ideal candidates for treatment with long-acting FSH analogues include infertile males with hypogonadotropic hypogonadism, who typically require prolonged courses of gonadotropin therapy. This technology also provides a significant improvement over current methods for stimulating follicular maturation and egg production in a subject being treated for infertility and for in vitro fertilization protocols.

Example 2

The β-hFSH-N2/N4-α Fusion Protein

In vitro Bioactivity

The bioactivity of the β-hFSH-N2/N4-α analogues was first assessed by an assay for hFSH receptor activation as discussed above. The N2/N4 analogue induced a similar rise in cAMP levels when compared with native hFSH, demonstrating that, like the CTP analogue discussed above, this single-chain fusion protein folded properly into an unhindered, biologically active hormone.

Pharmacokinetics

Figure 18:
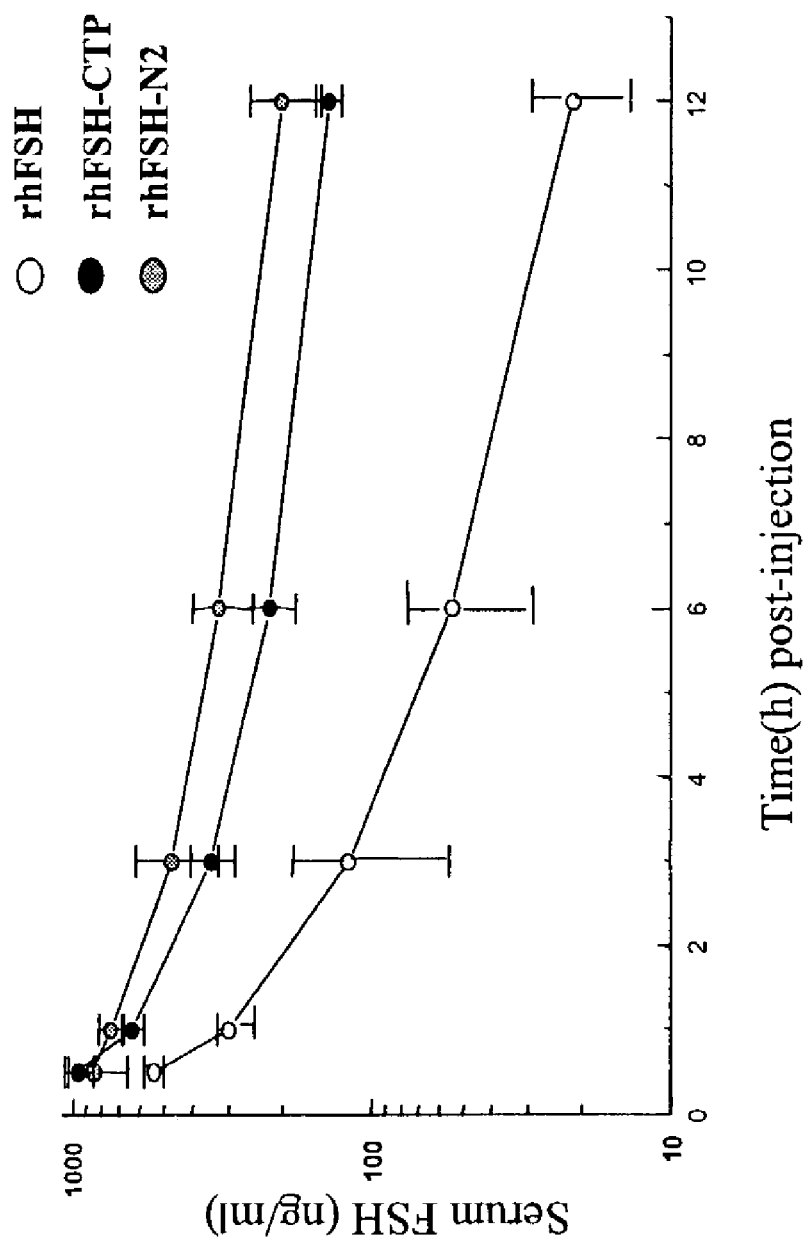
FIG. 18: Mean serum hFSH concentration-time profiles following a single IV injection of either recombinant human FSH (rFSH, bottom), FSH-CTP (middle) or N-2 (top). Twenty-one day old female rats were injected at a dose of 2800 ng/rat.

Pharmacokinetic analysis was performed using twelve immature female rats divided into four groups of 3 each. Each of the three proteins (hFSH, hFSH-CTP, hFSH-N2) was diluted to 11 μg/ml in injection buffer containing BSA (1 mg/ml), and given as a single intravenous dose of 2800 ng/rat in 0.25 ml of buffer. The control group received 0.25 ml of saline (data not shown). Serum was assayed at the following intervals post-injection: 0.5, 1.0, 3.0, 6.0, and 12 hours. The serum concentration-time curves are shown in FIG. 18. For all products the curves could be explained by a two-compartment model, with an initial half-life reflecting the distribution phase, and a second, slower elimination half-life. As indicated by the pharmacokinetic parameter estimates in Table 3, the half-life of elimination for the synthetic FSHs, hFSH-CTP and hFSH-N2, was approximately two-fold longer than that of native hFSH (3.5 h vs 7.1 and 6.3 h, respectively).

TABLE 3

Mean pharmacokinetic parameter estimates after IV bolus injection of rhFSH, rhFSH-CTP or hFSH-N2, each at a dose of 2800 ng/rat (n = 3). AUC = area under the curve.

| PARAMETER | rhFSH | rhFSH-CTP | rhFSH-N2 |
|---|---|---|---|
| $AUC_{0-infinity}$ (ng/hr/ml) | 1491 | 3887 | 4802 |
| $T_{1/2\ elimination}$ (hr) | 3.7 | 7.1 | 7.3 |
| Clearance (ml/hr) | 1.9 | 0.72 | 0.58 |

In vivo Bioactivity

Figure 17:
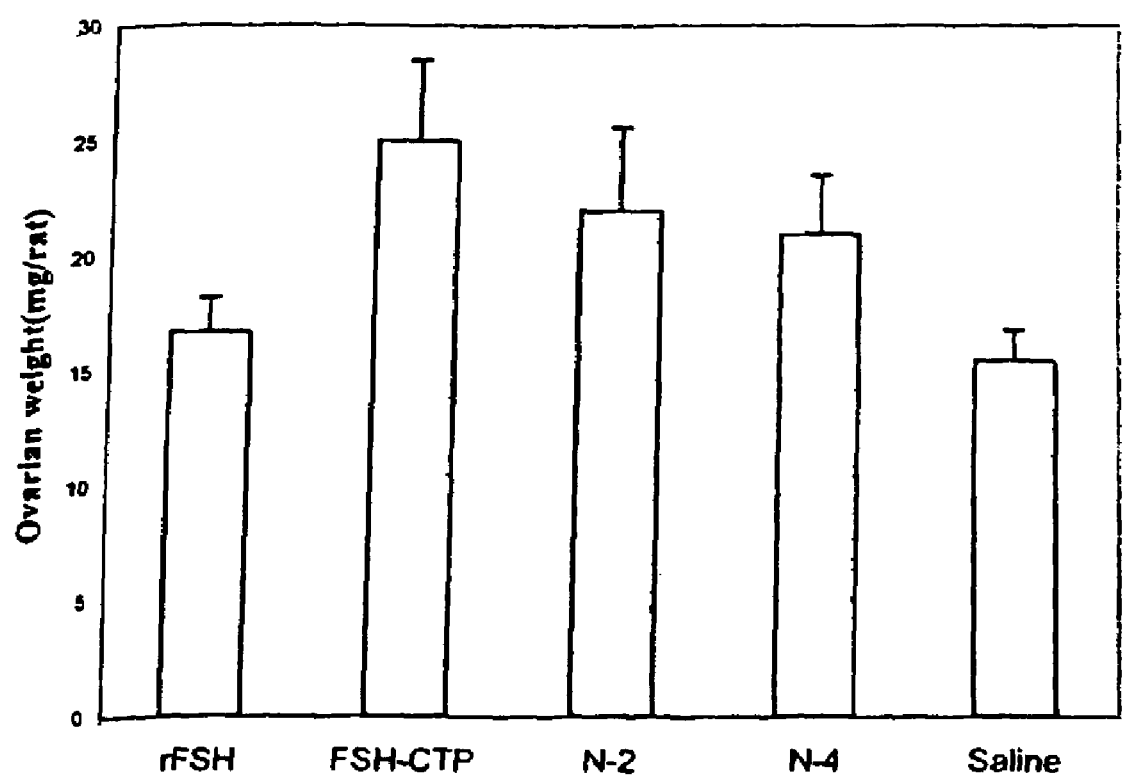
FIG. 17: Mean ovarian weight three days following subcutaneous injection of either recombinant human FSH (rFSH), FSH-CTP, N-2, N4, or saline.

An ovarian weight gain assay was used to assess the relative in vivo bioactivity of the control, recombinant native FSH (rFSH) and the CTP and N2 FSH analogues. The compounds were administered in a single subcutaneous injection. The mean ovarian weights as determined on day three following injection are shown in FIG. 17.

Pharmacodynamics

The pharmacodynamics of the N2/N4 analogues were assessed by a determination of ovarian weight change in immature female rats following a single subcutaneous injection of either a recombinant native hFSH, the CTP, the N2, or the N4 analogue. The results of these analyses are summarized in FIG. 19. The data indicated that the mean ovarian weights three days post-injection were significantly higher for the CTP, N2 and N4 analogues compared with the native hFSH control or saline.

Conclusions

The results described herein demonstrate that the addition of N-linked carbohydrates imparts a longer half-life to native hFSH, thereby increasing its bioactivity in a manner analogous to that conferred by the O-linked sugars on the CTP.

These results further demonstrate that a synthetic sequence bearing artificial N-linked glycosylation consensus sequences can be efficiently glycosylated in cultured cells. This in turn demonstrates the feasibility of producing synthetic FSH having improved stability and bioactivity through directed modifications of glycosylation patterns via the addition of artificial sequences.

Example 3

The VEGF-β-hFSH-CTP-α Fusion Protein

In vitro Bioactivity

Figure 19:
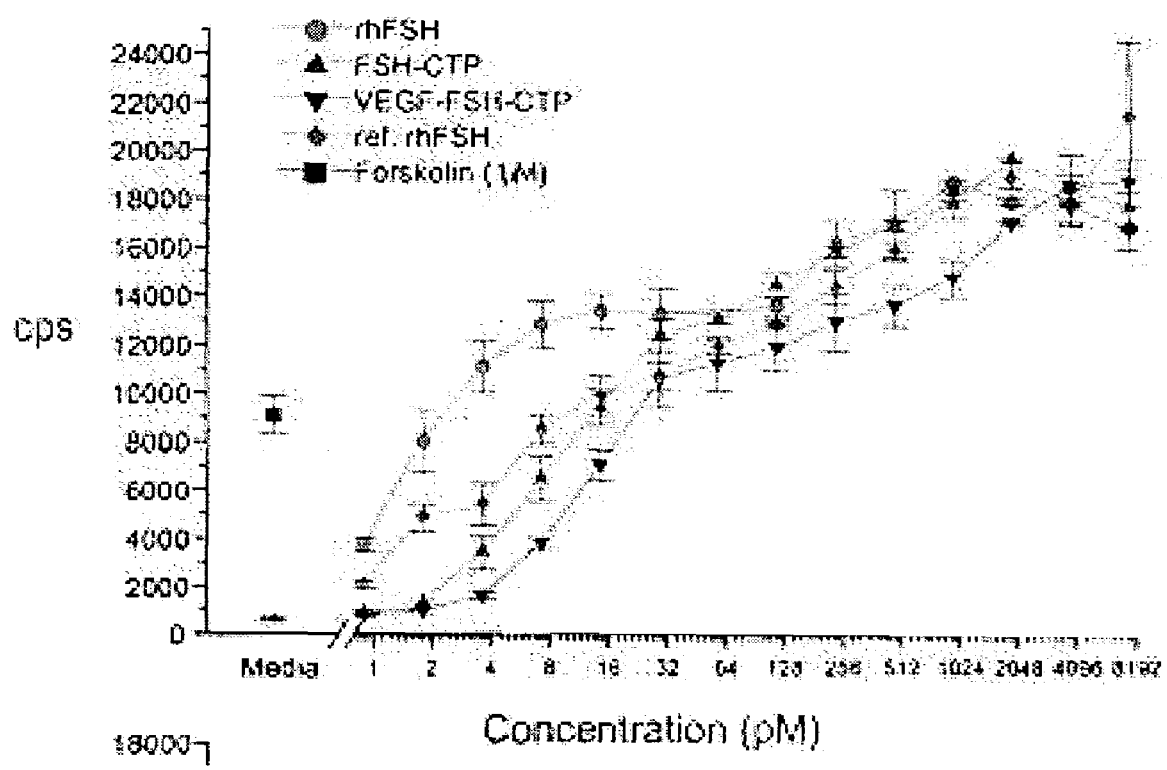
FIG. 19: In vitro bioactivity of VEGF-FSH (inverted triangle), recombinant native hFSH (circle and diamond), synthetic FSH-CTP (triangle).

Purified VEGF-FSH was tested for both FSH and VEGF activity. In vitro FSH activity was examined using a cell line expressing the hFSH receptor as described in the methods section. As shown in FIG. 19, the VEGF-FSH fusion protein exhibited similar in vitro bioactivity compared to recombinant hFSH.

The biological activity of the VEGF portion of the chimera, was confirmed in a number of in vitro assays. First, the ability of VEGF-FSH to stimulate the proliferation of endothelial cells was evaluated using an MTT assay. The MTT assay measures metabolic activity which is used here as an indicator of cell proliferation. The ability of the synthetic VEGF-FSH to proliferate human micro vascular endothelial cells is demonstrated in FIG. 20A. Notably, metabolism as determined with the MTT assay was directly proportional to the concentration of the VEGF-FSH fusion protein in the media. The response observed was similar to that induced by the same concentrations of commercially available preparations of VEGF (Becton Dickinson Labware, Franklin Lakes, N.J.).

The supernatant of CHO cells transfected with the VEGF-FSH fusion protein was also examined for its effects on cell metabolism in the MTT assay. As shown in FIG. 20B, supernatant from VEGF-FSH-secreting cells induced a response comparable to that of complete medium which is rich in numerous growth factors (EBM plus VEGF, hFGF-β, hEGF and R3-IGF-1; growth factors supplied by Clonetics and added in concentrations specified by the manufacturer). In contrast, the supernatant of cells secreting synthetic FSH-CTP alone induced only a modest response, indicating that the VEGF component is active and contributing significantly to the response observed with-the VEGF-FSH fusion protein.

Figure 21:
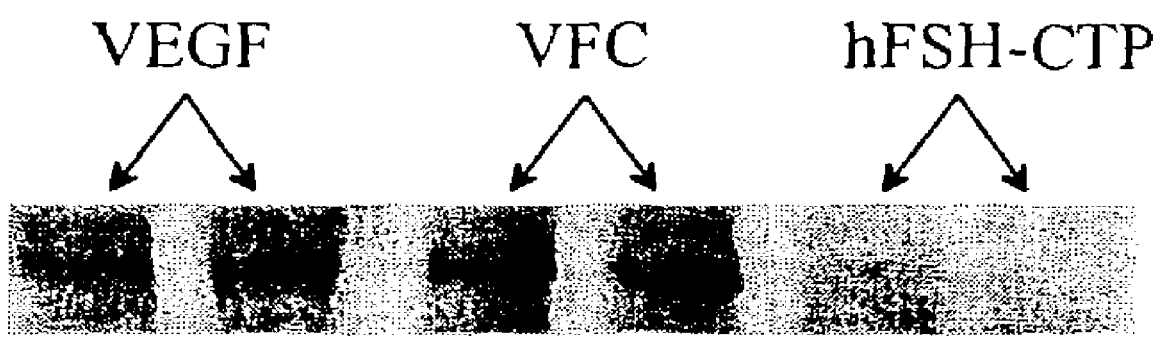
FIG. 21: Phosphorylation of VEGF receptor. Cells were incubated with either native VEGF, VEGF-FSH (VFC), or synthetic FSH-CTP (hFSH-CTP), as indicated by arrows.

The primary molecular response elicited by a growth factor is the autophosphorylation of its cognate receptor, which is induced upon ligand binding. Therefore, the ability of VEGF-FSH to induce phosphorylation of the VEGF receptor was tested. Western blotting and immunodetection with phosphotyrosine-specific antibodies was used to detect the phosphorylation state of the receptor. As illustrated in FIG. 21, cells treated with VEGF-FSH induced a level of receptor phosphorylation similar to that induced by native VEGF. The absence of receptor phosphorylation in cells treated with hFSH-CTP indicates that the observed phosphorylation is due to of the VEGF portion of our chimeric molecule.

In vivo Bioactivity

Figure 22:
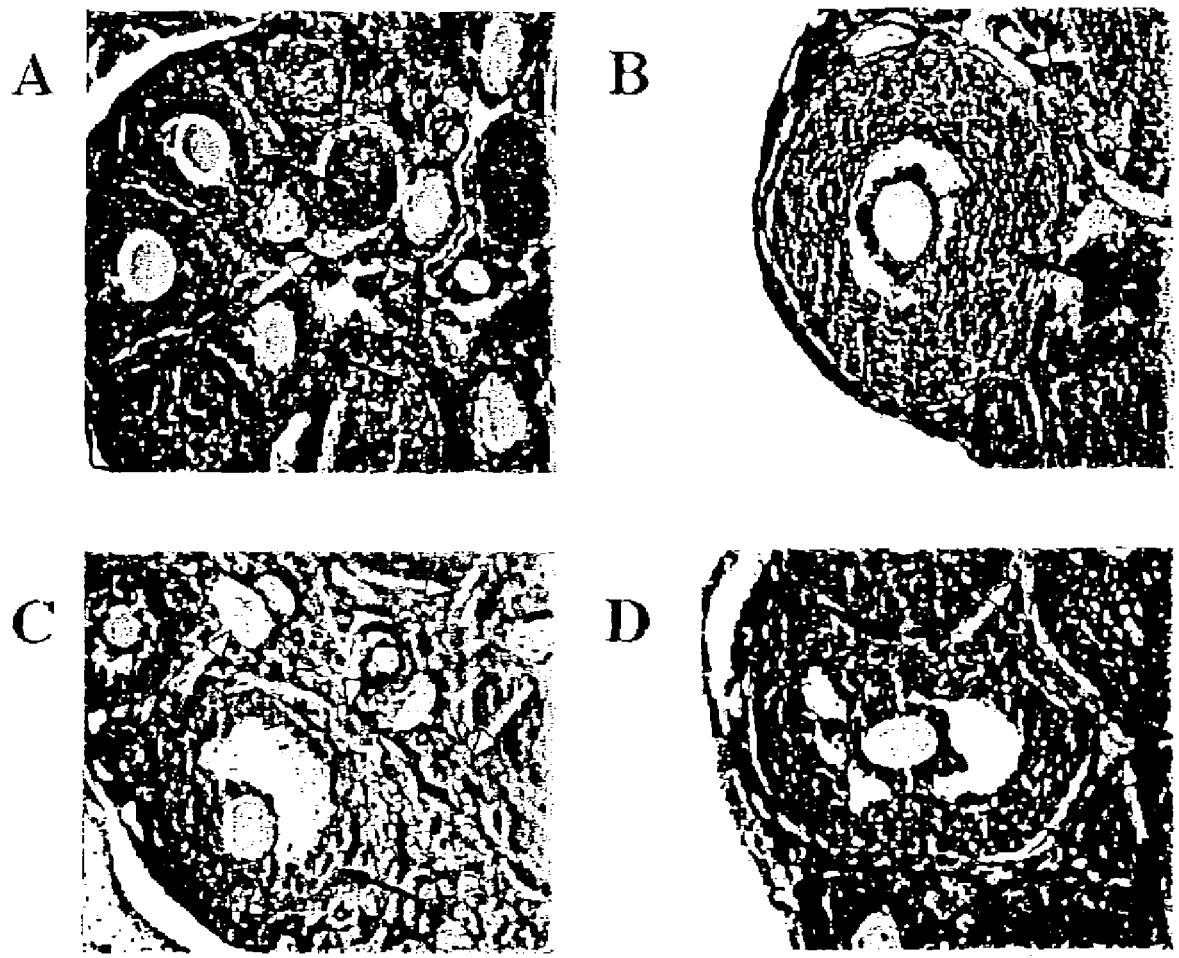
FIG. 22: Ovarian H&E sections taken from mice injected with either saline (Panel A), synthetic FSH-CTP (Panel B), VEGF-FSH (Panel C), or a mixture of FSH-CTP and native VEGF (Panel D).

The in viva bioactivity of the VEGF-FSH fusion protein was evaluated by examining its effects on follicular development in mice. Immature, hypophysectomized female mice were used in these studies because they lack appreciable endogenous FSH. The ovaries of hypophysectomized female mice were harvested for analysis four days following a single subcutaneous injection of either saline, hFSH-CTP, VEGF-FSH, or both hFSH-CTP and VEGF administered together. As shown in FIG. 22, induction of follicular maturation was evident in all groups except that receiving saline. The presence of stage 6-7, preantral to early antral, follicles is indicated in the figure by closed arrows. In contrast, animals from the saline control group 1 did not show progression beyond a stage 5 follicle, as indicated by multiple granulosa cell layers, but no early antrum formation. This is consistent with complete gonadotropin deprivation in this group.

Figure 23:
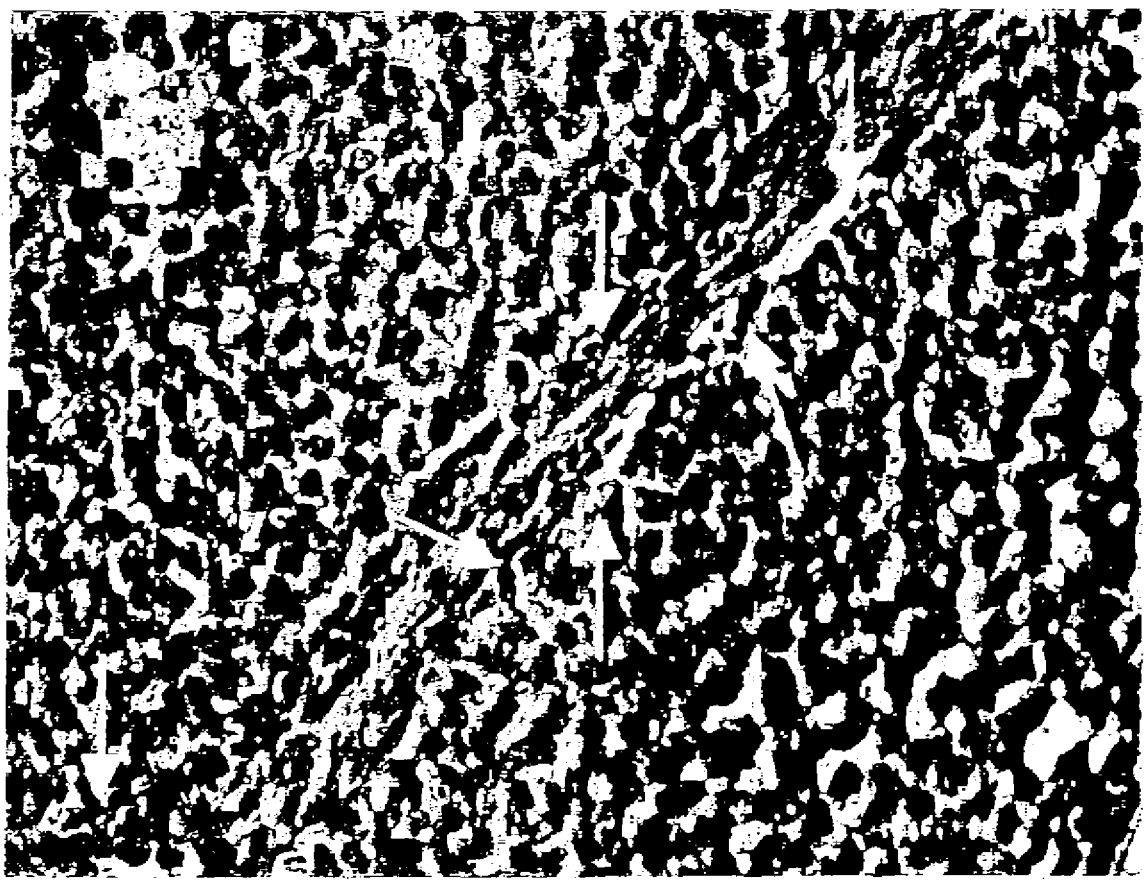
FIG. 23: Representative ovarian H&E section showing perifollicular capillaries (arrows).

Notably, stromal vessels taken from animals injected with VEGF-FSH were engorged compared with those from animals receiving either hFSH-CTP or the combination of VEGF and hFSH-CTP (FIG. 23, open arrows). Perifollicular capillary density was assessed as described in the methods section. A representative H&E section is shown in FIG. 23. The number of capillaries per square millimeter was 50 for saline, 300 for hFSH-CTP, 380 for VEGF-FSH and 300 for the combination of both hFSH-CTP and VEGF. These results indicate that the VEGF-FSH fusion protein achieved enhanced VEGF activity at the ovary compared to synthetic FSH alone and FSH-CTP plus free VEGF. Furthermore, these results indicate that the VEGF moiety of the VEGF-FSH fusion has an extended in vivo half-life compared to free VEGF.

Targeting of the VEGF-FSH-CTP

To test whether the VEGF activity of the single-chain VEGF-FSH-CTP chimera was systemic or whether VEGF activity was targeted to the ovary, adult mice were given a single injection of either: (1) saline (2) VEGF-FSH-CTP, (3) commercially available VEGF, or (4) VEGF-N2. No serious illness was noted in animals receiving commercially available VEGF, most likely due to its short half-life in vivo. In contrast, the animals receiving VEGF-N2 exhibited signs of lethargy, tachypnea, tachycardia, and generalized edema consistent with prolonged systemic VEGF activity. Surprisingly, animals receiving VEGF-FSH-CTP exhibited no gross adverse effects. Animals were sacrificed at 12 hours and 24 hours post-injection and the liver and pituitary were collected, sectioned, and evaluated via H&E staining for evidence of deleterious VEGF activity, such as micro- vascular bleeding. The results confirmed that the VEGF- FSH-CTP glycoprotein exhibited negligible extra-ovarian VEGF affects, even though it had a substantially increased half-life relative to native VEGF. Thus, the incorporation of the FSH moiety successfully promoted the localization of the VEGF-FSH-CTP glycoprotein at the target tissue.

Discussion

The data disclosed herein demonstrate the feasibility of producing multifunctional hormone analogues to achieve both improved in vivo stability and activity at the site of the target tissue. The single chain chimeric construct provided herein is a relatively large multidomain protein. These are the first demonstration that such a protein can be produced in a manner that retains the biological activity of each independent factor.

Multi-functional hFSH constructs are useful for targeting a bioactive protein to the ovary. This technique may be also be adapted to target factors to other tissues by replacing hFSH with other tissue-specific factors.

The results herein also demonstrate that a synthetic VEGF-hFSH-CTP protein can induce neovascularization as well as increase delivery of blood through existing ovarian vasculature. This will improve follicular recruitment and growth, processes known to be dependent on neovascuoarization and mediated, at least in part, by endogenous VEGF.

The methods described herein can also be used to tether other growth factors to hFSH, for example, to treat infertility. Particularly promising factors include TGFα and β1, EGF (epidermal growth factor), SCF (stem cell factor), IGF (insulin-like growth factor) I & II, and KGF (keratinocyte growth factor). For each of these factors the mature polypeptide that encodes the minimal domain necessary to exert an effect can be used for fusion with the hFSH-CTP construct.

The modularity of this approach allows different orientations to be used to achieve maximal activity. For growth factors such as EGF or TGF-β1, wherein the mature peptide is buried within a much larger pro-protein, the signal sequence of the β-hFSH subunit can be used to drive secretion.

For construction of other growth factor FSH fusion proteins, clones may either be acquired from the-American Type Culture Collection or the appropriate cDNAs may be isolated by RT-PCR from cell lines or tissues using standard techniques. Select domains may be synthesized for expression when the active polypeptide is small (e.g., EGF).

For example, an EGF-FSH fusion can be produced as follows. The small EGF cDNA encoding the 53 amino acids of the mature protein is isolated and ligated in-frame at the carboxy terminus of the hFSH-CTP clone. The hFSH α-subunit terminator codon is deleted while another terminator codon is added at the C-terminal end of EGF. An amino-terminal fusion is generated by placing the cDNA encoding the 53 residues of EGF between the signal peptide of the β-hFSH subunit and the first residue of the mature β-hFSH (while maintaining residues required for cleavage of the signal peptide). This sequence utilizes the signal peptide of β-hFSH to drive secretion in the absence of the signal sequence from EGF at the amino terminus of the fusion protein.

TGF α and β1 fusion proteins may be produced using a methodology analogous to that used for EGF. For example, the cDNA encoding the 50 residues of the mature TGFα and that encoding the 112 residues of the mature TGFβ1 can be fused to the hFSH-CTP molecule at the amino and carboxy terminal ends. Again, the signal sequence of the β-hFSH moiety is used to drive secretion of the amino terminal fusions by placing the growth factors between the β-hFSH signal sequence and the first residue of the mature β-hFSH polypeptide.

By way of further example, an IGF-FSH-CTP fusion can be made by ligating the 70 and 67 residue active polypeptides of IGF I and II, respectively, to FSH-CTP by either of two methods. In the first, a cDNA encoding the active domains is inserted into the FSH-CTP clone as described for EGF and TGFα and β1. Alternatively, IGF can be tethered to the FSH-CTP at the amino terminus using its native signal sequences and removing the signal sequence form the β-hFSH moiety as was described for the VEGF-FSH construct.

An SCF-hFSH-CTP fusion can be made as described for IGF I and II. However, this SCF possesses both soluble and membrane associated domains. The transmembrane and intracellular domains are at the carboxy terminus of the protein. Therefore the expressed protein is truncated to consist of the 165 residues comprising the mature, active, soluble peptide. Thus, the SCF protion of the fusion construct terminates at the sequence: ASSLR. Alternatively, the native signal sequence of SCF may be used for secretion if an additional 25 residues are included at the amino terminus of the polypeptide.

A final example is the KGF-FSH-CTP fusion, in which a cDNA encompassing the entire coding domain (582 bp) is fused to hFSH-CTP at the amino terminus utilizing the signal sequence of KGF to drive secretion of the fusion protein. This linkage sequence removes the signal sequence from hFSH-CTP as was described for the VEGF-FSH fusion. Alternatively, a carboxy-terminal fusion of the 163 residue mature KGF protein can be made. The terminator codon of the C-terminal α-subunit is removed and placed instead after the KGF domain.

All of the above fusions include a Ser-Gly tether between the growth factor and the hFSH-CTP. This flexible tether alleviates any inhibitory steric effects resulting from the close proximity of the active domains of these multidomain fusion proteins.

Naturally, the production of tissue-directed molecular therapy has applications beyond infertility. Localization of VEGF to the heart after cardiac infarction or to skin for improved would-healing are also potential candidates for this type of therapy. Numerous other therapies to target other growth factors to specific tissues of interest may also be worthwhile. Our therapeutic design avoids many of the complications of gene therapy, like exposure to viral constructs to carry the gene of interest, difficulty with tissue specificity, and inefficiency of genomic integration. In summary, we have shown that through the use of hyper-glycosylation to improve half-life and careful protein design, the creation of biologically active, tissue-specific fusion proteins is possible.

REFERENCES

Bouloux, P. M., D. J. Handelsman, F. Jockenhovel, E. Nieschlag, J. Rabinovici, W. L. Frasa, J. J. de Bie, G. Voortman, and J. Itskovitz-Eldor (2001) First human exposure to FSH-CTP in hypogonadotrophic hypogonadal males. *Hum. Reprod.* 16, 1592-1597.

Calvo, F. O., H. T. Keutmann, E. R. Bergert, and R. J. Ryan (1986) Deglycosylated human follitropin: characterization and effects on adenosine cyclic 3', 5'-phosphate production in porcine granulosa cells. *Biochemistry* 25, 3938-3943.

Chui, D. K., N. D. Pugh, S. M. Walker, L. Gregory, and R. W. Shaw (1997) Follicular vascularity-the predictive value of transvaginal power Doppler ultrasonography in an in vitro fertilization programme: a preliminary study. *Hum. Reprod.* 12, 191-196.

Dissen, G. A., H. E. Lara, W. H. Fahrenbach, M. E. Costa, and S. R. Ojeda (1994) Immature rat ovaries become revascularized rapidly after autotransplantation and show a gonadotropin-dependent increase in angiogenic factor gene expression. *Endocrinology* 134, 1146-1154.

Fares, F. A., N. Suganuma, K. Nishimori, P. S. Lapolt, A. J. Hsueh, and I. Boime (1992) Design of a long-acting follitropin agonist by fusing the C-terminal sequence of the chorionic gonadotropin beta subunit to the follitropin beta subunit. *Proc. Natl. Acad. Sci. U.S.A.* 89, 4304-4308.

Feng, W., M. M. Matzuk, K. Mountjoy, E. Bedows, R. W. Ruddon, and I. Boime (1995) The asparagine-linked oligosaccharides of the human chorionic gonadotropin beta subunit facilitate correct disulfide bond pairing. *J. Biol. Chem.* 270, 11851-11859.

Ferrara, N., K. Houck, L. Jakeman, and D. W. Leung (1992) Molecular and biological properties of the vascular endothelial growth factor family of proteins. *Endocr. Rev.* 13, 18-32.

Ferrara, N., H. Chen, T. Davis-Smyth, H. P. Gerber, T. N. Nguyen, D. Peers, V. Chisholm, K. J. Hillan, and R. H. Schwall (1998) Vascular endothelial growth factor is essential for corpus luteum angiogenesis. *Nat. Med.* 4, 336-340.

Krichevsky, A., S. Birken, J. F. O'Connor, K. Bikel, J. Schlatterer, and R. E. Canfield (1994) The development of a panel of monoclonal antibodies to human luteinizing hormone and its application to immunological mapping and two-site assays. *Endocrine* 2, 511-520.

LeContonnec, J. Y., H. C. Porchet, V. Beltrami, A. Khan, S. Toon, and M. Rowland (1994) Clinical pharmacology of recombinant human follicle-stimulating hormone. II. Single doses and steady-state pharmacokinetics. *Fertil. Steril.* 61, 679-86.

Lindau-Shapard, B. A., H. A. Brumberg, A. J. Peterson, and J. A. Dias (2001) Reversible immunoneutralization of human follitropin receptor. *J. Reprod. Immun.* 49, 1-19.

Matzuk, M. M., J. L. Keene, and I. Boime (1989) Site specificity of the chorionic gonadotropin N-linked oligosaccharides in signal transduction. *J. Biol. Chem.* 264, 2409-2414.

Matzuk, M. M., A. J. Hsueh, P. Lapolt, A. Tsafriri, J. L. Keene, and I. Boime (1990) The biological role of the carboxyl-terminal extension of human chorionic gonadotropin beta-subunit. *Endocrinology* 126, 376-383.

Nargund, G., T. Bourne, P. Doyle, J. Parsons, W. Cheng, S. Campbell, and W. Collins (1996) Associations between ultrasound indices of follicular blood flow, oocyte recovery and preimplantation embryo quality. *Hum. Reprod.* 11, 109-113.

Pedersen, T. and H. Peters (1968) Proposal for a classification of oocytes and follicles in the mouse ovary. *J. Reprod. Fertil* 17, 555-557.

Pierce, J. G. and T. F. Parsons (1981) Glycoprotein hormones: structure and function. *Annu. Rev. Biochem.* 50, 465-495.

Porchet, H. C., J. Y. LeContonnec, B. Neuteboom, S. Canali, and G. Zanolo (1995) Pharmacokinetics of recombinant human luteinizing hormone. *J. Clin. Endocrinol. Metab.* 80, 667-73.

Saal, W., H. J. Glowania, and J. Happ (1991) Pharmacodynamics and pharmacokinetics after subcutaneous and intramuscular injection of human chorionic gonadotropin. *Fertil. Steril.* 56, 225-8.

Sairam, M. R. and P. Manjunath (1982) Studies on pituitary follitropin. XL Induction of hormonal antagonistic activity by chemical deglycosylation. *Mol. Cell Endocrinol.* 28, 139-150.

Sugahara, T., M. R. Pixley, F. Fares, and I. Boime (1996) Characterization of the O-glycosylation sites in the chorionic gonadotropin beta subunit in vivo using site-directed mutagenesis and gene transfer. *J. Biol. Chem.* 271, 20797-20804.

Suganuma, N., M. M. Matzuk, and I. Boime (1989) Elimination of disulfide bonds affects assembly and secretion of the human chorionic gonadotropin beta subunit. *J. Biol. Chem.* 264, 19302-19307.

Van Blerkom, J., M. Antczak, and R. Schrader (1997) The developmental potential of the human oocyte is related to the dissolved oxygen content of follicular fluid: association with vascular endothelial growth factor levels and perifollicular blood flow characteristics. *Hum. Reprod.* 12, 1047-1055.

Vecchi, A., C. Garlanda, M. G. Lampugnani, M. Resnati, C. Matteucci, A. Stoppacciaro, H. Schnurch, W. Risau, L. Ruco and A. Mantovani (1994) Monoclonal antibodies specific for endothelial cells of mouse blood vessels. Application in the identification of adult and embryonic endothelium. *Eur. J. Cell Biol.* 63, 247-254.

Yen, S. S., O. Llerena, B. Little, and O. H. Pearson (1968) Disappearance rates of endogenous luteinizing hormone and chorionic gonadotropin in man. *J. Clin. Endocrinol. Metab* 28, 1763-1767.

SEQUENCE LISTING

```
<160> NUMBER OF SEQ ID NOS: 9

<210> SEQ ID NO 1
<211> LENGTH: 441
<212> TYPE: DNA
<213> ORGANISM: human
<220> FEATURE:
<221> NAME/KEY: misc_feature
<223> OTHER INFORMATION: hFSHb-N2

<400> SEQUENCE: 1
atgaagacac tccagttttt cttccttttc tgttgctgga aagcaatctg ctgcaatagc      60
tgtgagctga ccaacatcac cattgcaata gagaaagaag aatgtcgttt ctgcataagc     120
atcaacacca cttggtgtgc tggctactgc tacaccaggg atctggtgta taaggaccca     180
gccaggccca aaatccagaa aacatgtacc ttcaaggaac tggtatatga aacagtgaga     240
gtgcccggct gtgctcacca tgcagattcc ttgtatacat acccagtggc cacccagtgt     300
cactgtggca agtgtgacag cgacagcact gattgtactg tgcgaggcct ggggcccagc     360
tactgctcct ttggtgaaat gaaagaagga tccggatcga acgcgacggg gtcaggttct     420
aatgcaactt caggatccta a                                               441

<210> SEQ ID NO 2
<211> LENGTH: 486
<212> TYPE: DNA
<213> ORGANISM: human
<220> FEATURE:
<221> NAME/KEY: misc_feature
<223> OTHER INFORMATION: hFSHb-N4

<400> SEQUENCE: 2
atgaagacac tccagttttt cttccttttc tgttgctgga aagcaatctg ctgcaatagc      60
tgtgagctga ccaacatcac cattgcaata gagaaagaag aatgtcgttt ctgcataagc     120
atcaacacca cttggtgtgc tggctactgc tacaccaggg atctggtgta taaggaccca     180
gccaggccca aaatccagaa aacatgtacc ttcaaggaac tggtatatga aacagtgaga     240
gtgcccggct gtgctcacca tgcagattcc ttgtatacat acccagtggc cacccagtgt     300
```

| | |
|---|---|
| cactgtggca agtgtgacag cgacagcact gattgtactg tgcgaggcct ggggcccagc | 360 |
| tactgctcct ttggtgaaat gaagaagga tccggatcga acgcgacggg gtcaggttct | 420 |
| aatgcaactt caagatccgg atcgaacgcg acggggtcag gttctaatgc aacttcagga | 480 |
| tcctaa | 486 |

<210> SEQ ID NO 3
<211> LENGTH: 777
<212> TYPE: DNA
<213> ORGANISM: human
<220> FEATURE:
<221> NAME/KEY: misc_feature
<223> OTHER INFORMATION: hFSHb-CTP-alpha

<400> SEQUENCE: 3

| | |
|---|---|
| atgaagacac tccagttttt cttccttttc tgttgctgga aagcaatctg ctgcaatagc | 60 |
| tgtgagctga ccaacatcac cattgcaata gagaaagaag aatgtcgttt ctgcataagc | 120 |
| atcaacacca cttggtgtgc tggctactgc tacaccaggg atctggtgta taggaccca | 180 |
| gccaggccca aaatccagaa acatgtacc ttcaaggaac tggtatatga acagtgaga | 240 |
| gtgcccggct gtgctcacca tgcagattcc ttgtatacat acccagtggc cacccagtgt | 300 |
| cactgtggca agtgtgacag cgacagcact gattgtactg tgcgaggcct ggggcccagc | 360 |
| tactgctcct ttggtgaaat gaagaagga tccccccgct tccaggactc ctcttcctca | 420 |
| aaggcccctc cccccagcct tccaagccca tcccgactcc cggggccctc ggacaccccg | 480 |
| atcctcccac aaactagtgc tcctgatgtg caggattgcc cagaatgcac gctacaggaa | 540 |
| aacccattct ctcccagcc gggtgcccca atacttcagt gcatgggctg ctgcttctct | 600 |
| agagcatatc ccactccact aaggtccaag aagacgatgt tggtccaaaa gaacgtcacc | 660 |
| tcagagtcca cttgctgtgt agctaaatca tataacaggg tcacagtaat gggggggttc | 720 |
| aaagtggaga accacggc gtgccactgc agtacttgtt attatcacaa atcttaa | 777 |

<210> SEQ ID NO 4
<211> LENGTH: 723
<212> TYPE: DNA
<213> ORGANISM: human
<220> FEATURE:
<221> NAME/KEY: misc_feature
<223> OTHER INFORMATION: hFSH-N2-alpha

<400> SEQUENCE: 4

| | |
|---|---|
| atgaagacac tccagttttt cttccttttc tgttgctgga aagcaatctg ctgcaatagc | 60 |
| tgtgagctga ccaacatcac cattgcaata gagaaagaag aatgtcgttt ctgcataagc | 120 |
| atcaacacca cttggtgtgc tggctactgc tacaccaggg atctggtgta taggaccca | 180 |
| gccaggccca aaatccagaa acatgtacc ttcaaggaac tggtatatga acagtgaga | 240 |
| gtgcccggct gtgctcacca tgcagattcc ttgtatacat acccagtggc cacccagtgt | 300 |
| cactgtggca agtgtgacag cgacagcact gattgtactg tgcgaggcct ggggcccagc | 360 |
| tactgctcct ttggtgaaat gaagaagga tccggatcga acgcgacggg gtcaggttct | 420 |
| aatgcaactt caggatccac tagtgctcct gatgtgcagg attgcccaga atgcacgcta | 480 |
| caggaaaacc cattcttctc ccagccgggt gccccaatac ttcagtgcat gggctgctgc | 540 |
| ttctctagag catatcccac tccactaagg tccaagaaga cgatgttggt ccaaaagaac | 600 |
| gtcacctcag agtccacttg ctgtgtagct aaatcatata acagggtcac agtaatgggg | 660 |
| ggtttcaaag tggagaacca cacggcgtgc cactgcagta cttgttatta tcacaaatct | 720 |

```
taa                                                                  723
```

<210> SEQ ID NO 5
<211> LENGTH: 768
<212> TYPE: DNA
<213> ORGANISM: human
<220> FEATURE:
<221> NAME/KEY: misc_feature
<223> OTHER INFORMATION: hFSH-N4-alpha

<400> SEQUENCE: 5

```
atgaagacac tccagttttt cttccttttc tgttgctgga aagcaatctg ctgcaatagc     60
tgtgagctga ccaacatcac cattgcaata gagaaagaag aatgtcgttt ctgcataagc    120
atcaacacca cttggtgtgc tggctactgc tacaccaggg atctggtgta taaggaccca    180
gccaggccca aaatccagaa acatgtacc ttcaaggaac tggtatatga acagtgaga      240
gtgcccggct gtgctcacca tgcagattcc ttgtatacat acccagtggc cacccagtgt    300
cactgtggca gtgtgacag cgacagcact gattgtactg tgcgaggcct ggggcccagc     360
tactgctcct ttggtgaaat gaagaagga tccggatcga acgcgacggg gtcaggttct     420
aatgcaactt caagatccgg atcgaacgcg acggggtcag gttctaatgc aacttcagga    480
tccactagtg ctcctgatgt gcaggattgc ccagaatgca cgctacagga aaacccattc    540
ttctcccagc cgggtgcccc aatacttcag tgcatgggct gctgcttctc tagagcatat    600
cccactccac taaggtccaa gaagacgatg ttggtccaaa agaacgtcac ctcagagtcc    660
acttgctgtg tagctaaatc atataacagg gtcacagtaa tggggggttt caaagtggag    720
aaccacacgg cgtgccactg cagtacttgt tattatcaca aatcttaa                768
```

<210> SEQ ID NO 6
<211> LENGTH: 145
<212> TYPE: PRT
<213> ORGANISM: human
<220> FEATURE:
<221> NAME/KEY: misc_feature
<223> OTHER INFORMATION: beta-hCG

<400> SEQUENCE: 6

```
Ser Lys Glu Pro Leu Arg Pro Arg Cys Arg Pro Ile Asn Ala Thr Leu
1               5                   10                  15

Ala Val Glu Lys Glu Gly Cys Pro Val Cys Ile Thr Val Asn Thr Thr
            20                  25                  30

Ile Cys Ala Gly Tyr Cys Pro Thr Met Thr Arg Val Leu Gln Gly Val
        35                  40                  45

Leu Pro Ala Leu Pro Gln Val Val Cys Asn Tyr Arg Asp Val Arg Phe
    50                  55                  60

Glu Ser Ile Arg Leu Pro Gly Cys Pro Arg Gly Val Asn Pro Val Val
65                  70                  75                  80

Ser Tyr Ala Val Ala Leu Ser Cys Gln Cys Ala Leu Cys Arg Arg Ser
                85                  90                  95

Thr Thr Asp Cys Gly Gly Pro Lys Asp His Pro Leu Thr Cys Asp Asp
            100                 105                 110

Pro Arg Phe Gln Asp Ser Ser Ser Lys Ala Pro Pro Pro Ser Leu
        115                 120                 125

Pro Ser Pro Ser Arg Leu Pro Gly Pro Ser Asp Thr Pro Ile Leu Pro
    130                 135                 140

Gln
```

-continued

```
<210> SEQ ID NO 7
<211> LENGTH: 390
<212> TYPE: DNA
<213> ORGANISM: human
<220> FEATURE:
<221> NAME/KEY: misc_feature
<223> OTHER INFORMATION: beta-hFSH

<400> SEQUENCE: 7
atgaagacac tccagttttt cttccttttc tgttgctgga aagcaatctg ctgcaatagc      60
tgtgagctga ccaacatcac cattgcaata gagaaagaag aatgtcgttt ctgcataagc     120
atcaacacca cttggtgtgc tggctactgc tacaccaggg atctggtgta taaggaccca     180
gccaggccca aaatccagaa aacatgtacc ttcaaggaac tggtatatga aacagtgaga     240
gtgcccggct gtgctcacca tgcagattcc ttgtatacat acccagtggc cacccagtgt     300
cactgtggca agtgtgacag cgacagcact gattgtactg tgcgaggcct ggggcccagc     360
tactgttcct tggtgaaat gaaagaataa                                       390

<210> SEQ ID NO 8
<211> LENGTH: 351
<212> TYPE: DNA
<213> ORGANISM: human
<220> FEATURE:
<221> NAME/KEY: misc_feature
<223> OTHER INFORMATION: alpha-hFSH

<400> SEQUENCE: 8
atggattact acagaaaata tgcagctatc tttctggtca cattgtcggt gtttctgcat      60
gttctccatt ccgctcctga tgtgcaggat tgcccagaat gcacgctaca ggaaaaccca     120
ttcttctccc agccgggtgc cccaatactt cagtgcatgg gctgctgctt ctctagagca     180
tatcccactc cactaaggtc caagaagacg atgttggtcc aaaagaacgt cacctcagag     240
tccacttgct gtgtagctaa atcatataac agggtcacag taatgggggg tttcaaagtg     300
gagaaccaca cggcgtgcca ctgcagtact tgttattatc acaaatctta a              351

<210> SEQ ID NO 9
<211> LENGTH: 16
<212> TYPE: PRT
<213> ORGANISM: human

<400> SEQUENCE: 9

Ser Gly Ser Asn Ala Thr Gly Ser Gly Ser Asn Ala Thr Ser Gly Ser
1               5                   10                  15
```

What is claimed is:

1. A method for increasing vascularization in a tissue by contacting the tissue with an amount of a composition of matter comprising (a) at least one subunit of a hormone or growth factor selected from the group consisting of VEGF, GH, TGFα, TGFβ1, EGF, FGF, SCF, IGF-I, IGF-II, GDF-9, KGF, GM-CSF, LIF, follistatin, a neurotropin, angiopoiten I or II, MCP-1 and (b) a serum half-life-increasing moiety, wherein the hormone or growth factor subunit and serum half-life-increasing moiety are covalently bound, and wherein the serum half-life-increasing moiety is a polypeptide comprising the amino acid sequence ser-gly-ser-asn-ala-thr-gly-ser-gly-ser-asn-ala-thr-ser-gly-ser (SEQ ID NO:9), effective to increase vascularization in the tissue.

* * * * *